(12) United States Patent
Bellows et al.

(10) Patent No.: US 11,173,009 B2
(45) Date of Patent: Nov. 16, 2021

(54) MEDICAL DEVICE SUPPORT SYSTEM HAVING HUB ACCESS OPENING

(71) Applicant: American Sterilizer Company, Mentor, OH (US)

(72) Inventors: Lance Clark Bellows, Painesville, OH (US); Christopher Roy Mohr, Mentor, OH (US)

(73) Assignee: American Sterilizer Company, Mentor, OH (US)

( * ) Notice: Subject to any disclaimer, the term of this patent is extended or adjusted under 35 U.S.C. 154(b) by 178 days.

(21) Appl. No.: 16/517,708

(22) Filed: Jul. 22, 2019

(65) Prior Publication Data

US 2020/0030058 A1 Jan. 30, 2020

Related U.S. Application Data

(60) Provisional application No. 62/702,943, filed on Jul. 25, 2018, provisional application No. 62/702,946, (Continued)

(51) Int. Cl.
| | |
|---|---|
| *A61B 90/50* | (2016.01) |
| *F16M 11/20* | (2006.01) |
| *F16D 65/14* | (2006.01) |
| *F16D 121/14* | (2012.01) |
| *F16D 65/06* | (2006.01) |

(52) U.S. Cl.
CPC ............ *A61B 90/50* (2016.02); *F16D 65/065* (2013.01); *F16D 65/14* (2013.01);
(Continued)

(58) Field of Classification Search
CPC . A61B 90/50; A61B 2090/508; F16D 65/065; F16D 65/14; F16D 2121/14; F16M 11/2014
See application file for complete search history.

(56) References Cited

U.S. PATENT DOCUMENTS

| | | |
|---|---|---|
| 1,761,933 A | 1/1928 | Olivier |
| 2,266,727 A | 5/1940 | Ambrose |
| (Continued) | | |

FOREIGN PATENT DOCUMENTS

| | | |
|---|---|---|
| DE | 102016005785 A1 | 11/2017 |
| EP | 1239805 A1 | 9/2002 |
| (Continued) | | |

OTHER PUBLICATIONS

International Search Report and Written Opinion for corresponding International Application PCT/US2019/042738 dated Dec. 5, 2019.
(Continued)

*Primary Examiner* — Anita M King
(74) *Attorney, Agent, or Firm* — Renner, Otto, Boisselle & Sklar, LLP

(57) ABSTRACT

A medical device support system including a central shaft, an extension arm, and a brake assembly. The extension arm has a support for a medical device and a hub at its proximal end mounted to the central shaft for pivotable movement about the central shaft. The brake assembly is secured in the hub for rotation therewith and includes first and second discrete arc shape clamp pieces configured to flex toward and away from each other to respectively increase and decrease a frictional braking force to the central shaft. The hub includes a hub access opening configured to allow passage therethrough of at least one of the arc shape clamp pieces.

25 Claims, 29 Drawing Sheets

Related U.S. Application Data filed on Jul. 25, 2018, provisional application No. 62/702,947, filed on Jul. 25, 2018, provisional application No. 62/702,948, filed on Jul. 25, 2018, provisional application No. 62/799,096, filed on Jan. 31, 2019, provisional application No. 62/799,100, filed on Jan. 31, 2019, provisional application No. 62/799,113, filed on Jan. 31, 2019, provisional application No. 62/799,202, filed on Jan. 31, 2019, provisional application No. 62/809,173, filed on Feb. 22, 2019, provisional application No. 62/825,078, filed on Mar. 28, 2019, provisional application No. 62/828,090, filed on Apr. 2, 2019.

(52) U.S. Cl.
CPC .... *F16M 11/2014* (2013.01); *A61B 2090/508* (2016.02); *F16D 2121/14* (2013.01)

(56) References Cited

U.S. PATENT DOCUMENTS

| | | |
|---|---|---|
| 4,200,407 A | 4/1980 | Bianco |
| 4,955,458 A | 9/1990 | Shellhause |
| 6,899,442 B2 * | 5/2005 | Howell .................. E04B 9/006 248/278.1 |
| 7,849,978 B2 | 12/2010 | Graham et al. |
| 10,835,346 B2 * | 11/2020 | Bellows ................ F16M 11/08 |
| 10,874,476 B2 * | 12/2020 | Bellows ................ F16D 49/16 |
| 10,993,778 B2 * | 5/2021 | Bellows ................ A61B 90/35 |
| 2002/0015296 A1 * | 2/2002 | Howell .................. E04B 9/006 362/11 |
| 2011/0303499 A1 | 12/2011 | Chandan et al. |
| 2017/0326738 A1 | 11/2017 | Christiansen et al. |

FOREIGN PATENT DOCUMENTS

| | | |
|---|---|---|
| FR | 1441338 A | 6/1966 |
| WO | 0145627 A1 | 6/2001 |
| WO | 2008112675 A1 | 9/2008 |

OTHER PUBLICATIONS

Nuvo Surgical Navigator™ Equipment, Management System, A2Z00507 Rev 00 dated Jun. 29, 2010.

\* cited by examiner

MEDICAL DEVICE SUPPORT SYSTEM HAVING HUB ACCESS OPENING

This application claims priority to U.S. Patent Application No. 62/702,943 filed Jul. 25, 2018; U.S. Patent Application No. 62/702,946 filed Jul. 25, 2018; U.S. Patent Application No. 62/702,947 filed Jul. 25, 2018; U.S. Patent Application No. 62/702,948 filed Jul. 25, 2018; U.S. Patent Application No. 62/799,096 filed Jan. 31, 2019; U.S. Patent Application No. 62/799,100 filed Jan. 31, 2019; U.S. Patent Application No. 62/799,113 filed Jan. 31, 2019; U.S. Patent Application No. 62/799,202 filed Jan. 31, 2019; U.S. Patent Application No. 62/809,173 filed Feb. 22, 2019; U.S. Patent Application No. 62/825,078 filed Mar. 28, 2019; and U.S. Patent Application No. 62/828,090 filed Apr. 2, 2019. These prior applications are incorporated herein by reference.

FIELD OF INVENTION

This application relates generally to a medical device suspension system or carry system for use in, for example, a hospital examination room, a clinic, a surgery room or an emergency room, and more particularly to a medical device support system that has a multi-piece brake assembly and a hub access opening that simplify assembly and field service.

BACKGROUND

Medical device suspension systems or carry systems are used in health treatment settings such as hospital examination rooms, clinics, surgery rooms and emergency rooms. These systems may suspend or support any variety of medical devices or components including surgical lights, supply consoles, patient monitors, camera detector heads, medical instruments, ventilator systems, suction devices, among others. The supports typically include a central shaft or support column that is suspended from the ceiling or mounted to a wall, and one or more generally horizontal extension arms mounted for rotational movement about the shaft. A frictional brake is provided near the pivot location of the extension arm that is operable to maintain the extension arm in the desired angular position and to permit angular adjustment by a suitable force against the extension arm. The extension arm can be rotatably adjusted about the column to a desired angular position to provide appropriate access to medical devices and components associated with the arm.

Most of the current support systems utilize mechanical radial braking devices to provide the required rotational performances of system components. The basic principle of these devices is that the force needed to achieve the desired level of frictional braking is applied in the radial direction, transverse or perpendicular to the axis of component rotation. One example is a clamp assembly that has a generally C-shape construction. The clamp assembly is installed over the central shaft and into a hub portion of the pivoting extension arm. An actuator, which may also be part of the hub, is used to urge opposite sides of the brake clamp toward and away from the shaft. This process creates a normal force between the brake clamp and the shaft, and provides necessary frictional force to control the pivotable movement of the arm around the shaft.

For some medical device suspension systems or carry systems, there remain various shortcomings, drawbacks, and disadvantages relative to certain applications. For example, the C-shape clamp assembly has a split ring structure that can only be installed by positioning the split ring at an upper end (or lower end) of the support shaft and sliding the ring to the appropriate axial position along the shaft, i.e. near the pivoting location of the extension arm. This typically is done in a factory prior to shipping and installing the system in a surgery room or clinic, since the brake assembly must already be located on the shaft prior to mounting the shaft to a support surface or prior to attaching the extension arm to the shaft. Servicing the brake assembly also can be problematic, since the support system must be disassembled to provide access to an upper or lower shaft end. This usually requires removal and transport of the system from its health treatment room to an appropriate service facility. The brake assembly of these medical device support systems therefore is not easily field replaceable/serviceable.

Accordingly, there remains a need for further contributions in this area of technology.

SUMMARY OF INVENTION

The application relates to a medical device support system that has a multi-piece brake assembly and a hub access opening configured to allow passage therethrough of the pieces that make up the multi-piece brake assembly, and therefore simplifies and adds efficiency to the factory assembly and field service of the medical device support system.

According to one aspect of the invention, a medical device support system includes a central shaft; an extension arm having a support for a medical device and a hub at its proximal end mounted to the central shaft for pivotable movement about the central shaft; and, a brake assembly secured in the hub for rotation therewith and including first and second discrete arc shape clamp pieces configured to flex toward and away from each other to respectively increase and decrease a frictional braking force to the central shaft. The hub includes a hub access opening configured to allow passage therethrough of at least one of the arc shape clamp pieces.

Embodiments of the invention may include one or more of the following additional features separately or in combination.

The brake assembly may include an actuator configured to flex the first and second clamp pieces toward and away from each other to respectively increase and decrease the frictional braking force to the central shaft.

The hub may include axially spaced first and second bearing mounts that house respective first and second pivot bearings mounted to the central shaft, and the hub access opening may be disposed axially between the first and second bearing mounts.

The hub access opening may have an arc shape in axial cross section and may have a radius that is substantially the same as a radius of an outer wall of the hub.

A radial gap may be provided between an inner periphery of the hub and an outer periphery of the first and second arc shape clamp pieces to allow the first and second arc shape clamp pieces to be moved radially between the inner periphery of the hub and the central shaft.

The hub access opening may protrude radially through a wall in the hub and may be configured to allow passage of the arc shape clamp piece radially therethrough until an arc shape liner of the arc shape clamp piece abuts or nearly abuts the central shaft.

On a circumferentially adjacent side of the hub access opening, an inner periphery of the hub and an outer periphery of the central shaft may define a space to allow the at least one arc shape clamp piece to be rotated at least partially about the central shaft.

Axially adjacent to the hub access opening an inner periphery of the hub and an outer periphery of the central shaft may define a space to allow the at least one arc shape clamp piece to be moved axially to a position axially adjacent to the hub access opening.

The inner periphery of the hub may define a radially protruding notch that is configured to receive a radially protruding tab of the at least one arc shape clamp piece, and the radially protruding notch may be axially adjacent to the hub access opening.

The brake assembly may be configured such that when the first and second clamp pieces are flexed toward each other to increase the frictional braking force to the central shaft, the first and second clamp pieces have an arc shape contact with the outer periphery of the central shaft.

According to another aspect of the invention, an extension arm for a medical device support system having a central shaft, includes a support for a medical device; a hub at a proximal end of the extension arm, the hub being mountable to the central shaft for pivotable movement about the central shaft; and, a brake assembly secured in the hub for rotation therewith and including first and second discrete arc shape clamp pieces configured to flex toward and away from each other to respectively increase and decrease a frictional braking force to the central shaft. The hub includes a hub access opening configured to allow passage therethrough of at least one of the arc shape clamp pieces.

Embodiments of the invention may include one or more of the following additional features separately or in combination.

The hub access opening and a radial extent of the arm may be diametrically opposed from one another.

The hub access opening may protrude radially through a wall of the hub and may be configured to allow passage of the arc shape clamp piece radially therethrough.

The hub access opening may have an axial height that is greater than the axial height of the arc shape clamp piece.

The hub access opening may have a width in axial cross section that is greater than a width of the arc shape clamp piece in axial cross section from a free end to a connecting end of the arc shape clamp piece.

The brake assembly may be secured in the hub in a position axially below and/or axially above the hub access opening.

The first and second arc shape clamp pieces may include respective liners made of a material selected from polyolefins, polyesters, acetals, polyamides, fluorinated polymers, vinyls, acrylics, polycarbonates, polyimides, polysulphones, and blends and alloys thereof.

The first and second arc shape clamp pieces may include unreinforced, semi-crystalline thermoplastic polyester based on polyethylene terephthalate (PET-P).

The first and second arc shape clamp pieces may include respective first and second polymer liners made of UHMW-PE.

According to another aspect of the invention, there is provided a method of installing a brake assembly in a medical device support system having a central shaft and an extension arm having a support for a medical device and a hub at its proximal end mounted to the central shaft for pivotable movement about the central shaft. The method includes providing first and second discrete arc shape clamp pieces of the brake assembly; inserting the first and second arc shape clamp pieces through a hub access opening in the hub of the extension arm; arranging the first and second arc shape clamp pieces relative to the central shaft to respectively increase and decrease a frictional braking force to the central shaft in response to flexural movement of the first and second arc shape clamp pieces; and, securing the brake assembly in the hub of the extension arm for rotation with the extension arm about the central shaft.

Embodiments of the invention may include one or more of the following additional features separately or in combination.

The inserting may include inserting the first and second arc shape clamp pieces radially through the hub access opening until an inner liner abuts or nearly abuts the central shaft.

The arranging may include rotating the first and second arc shape clamp pieces at least partially about the central shaft.

The arranging may include moving the first and second arc shape clamp pieces to a position axially adjacent to the hub access opening.

The arranging may include inserting first and second radially protruding tabs of the respective first and second arc shape clamp pieces into a radially protruding notch in the hub to a position axially adjacent to the hub access opening.

The arranging may include sliding axially the first and second arc shape clamp pieces relative to one another.

The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention.

DETAILED DESCRIPTION

Figure 1:
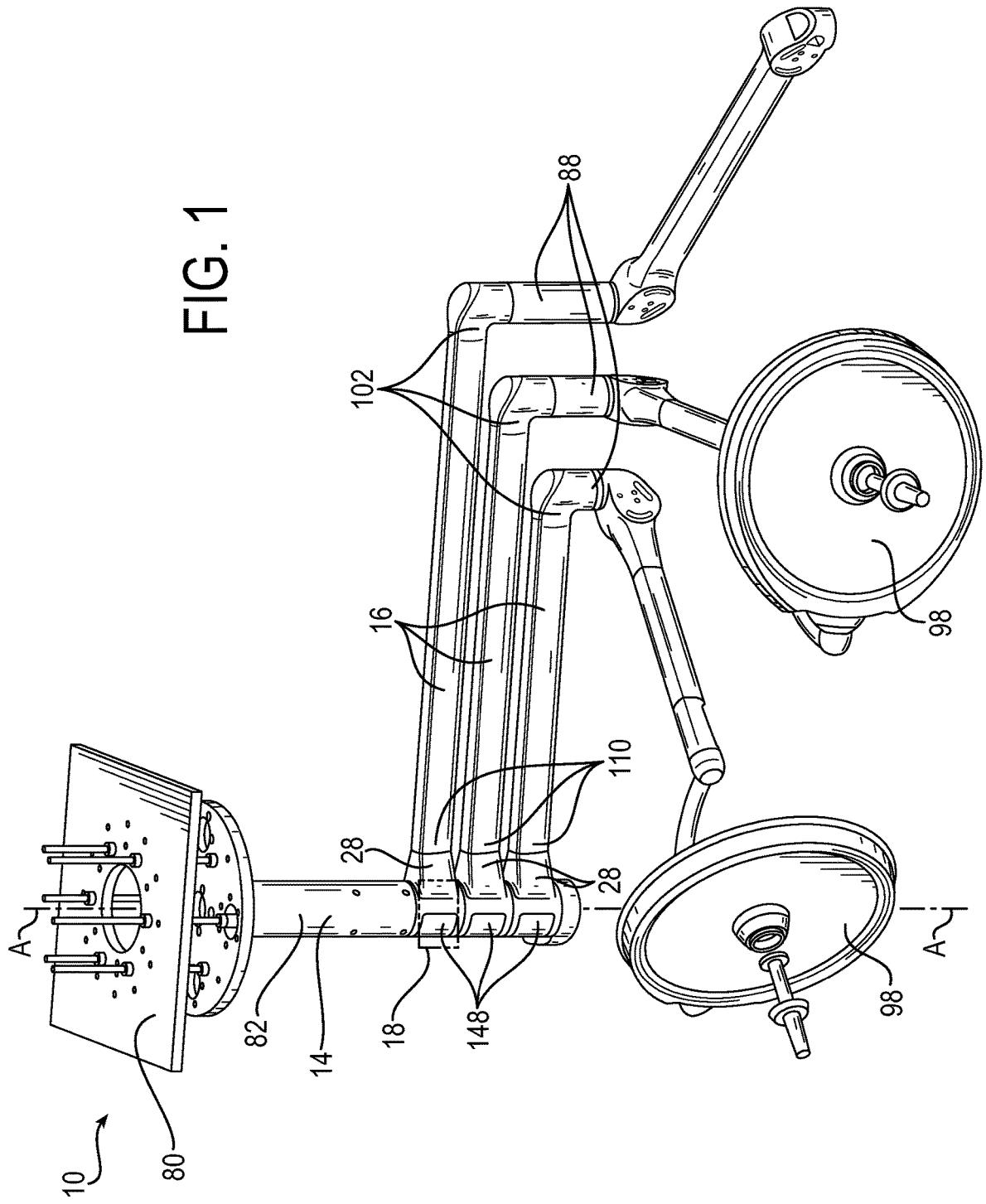
FIG. 1 is a perspective view of a medical device support system in accordance with an embodiment of the invention.

While the present invention can take many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications of the described embodiments, and any further applications of the principles of the invention as described herein, are contemplated as would normally occur to one skilled in the art to which the invention relates.

Figure 23:
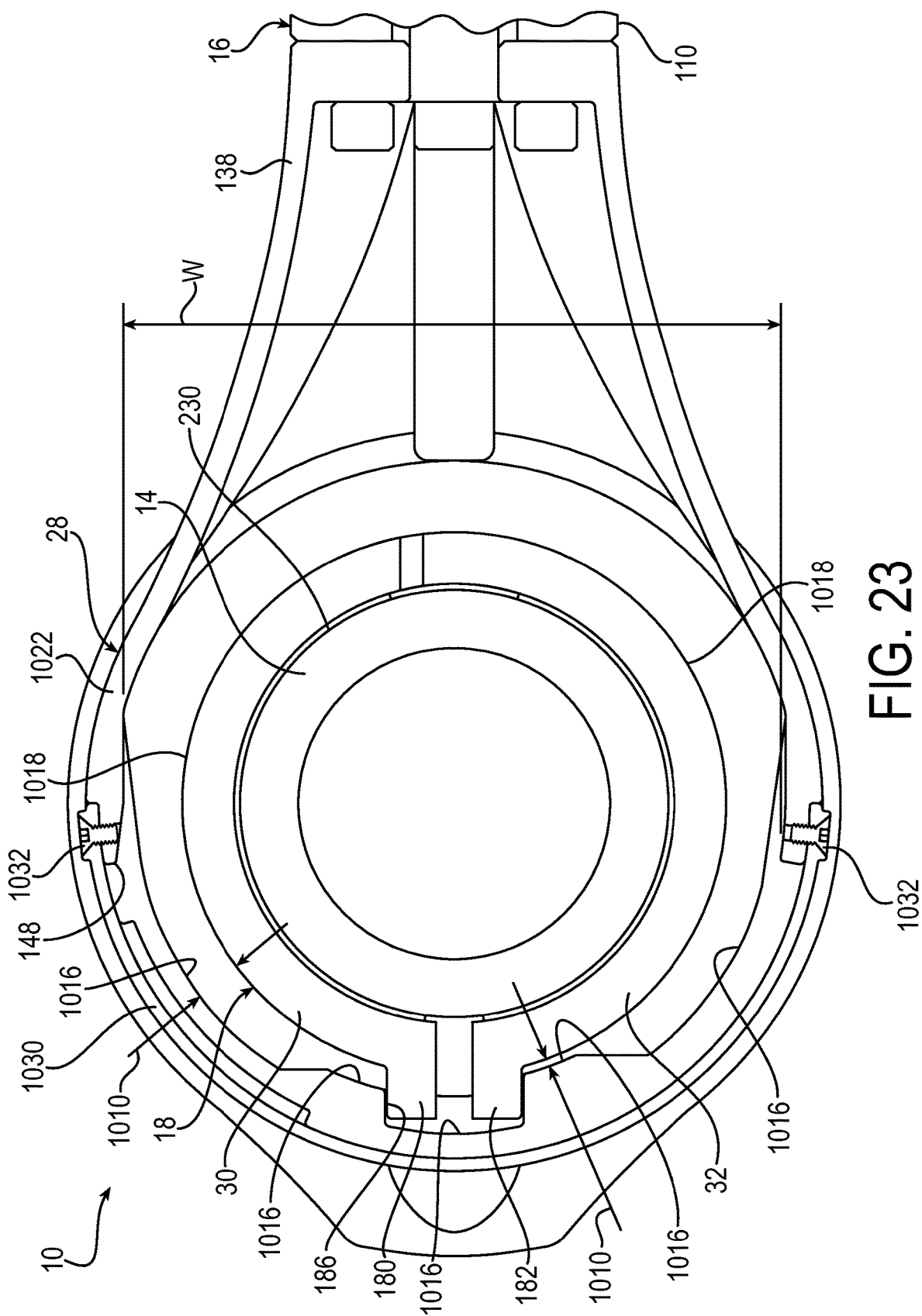
FIG. 23 is a cross-section view of the medical device support system of FIG. 1, as viewed from the plane 23-23 in FIG. 2, showing a hub access opening and a hub access opening cover panel.

FIGS. 1-14 show a medical device support system 10 that includes a central shaft 14, at least one extension arm 16 rotatably mounted to the shaft 14, and a brake assembly 18 secured in a hub 28 of the extension arm 16 for rotation with the extension arm 16. As shown in FIGS. 2, 4 and 23, the brake assembly 18 may include first and second discrete arc shape clamp pieces 30, 32 configured to flex toward and away from each other to respectively increase and decrease a frictional braking force to the central shaft 14. As will be described in greater detail below, the hub 28 includes a hub access opening 148 configured to allow passage therethrough of the first and second arc shape clamp pieces 30, 32, which simplifies and adds efficiency to the factory assembly and field service of the medical device support system 10.

Figure 2:
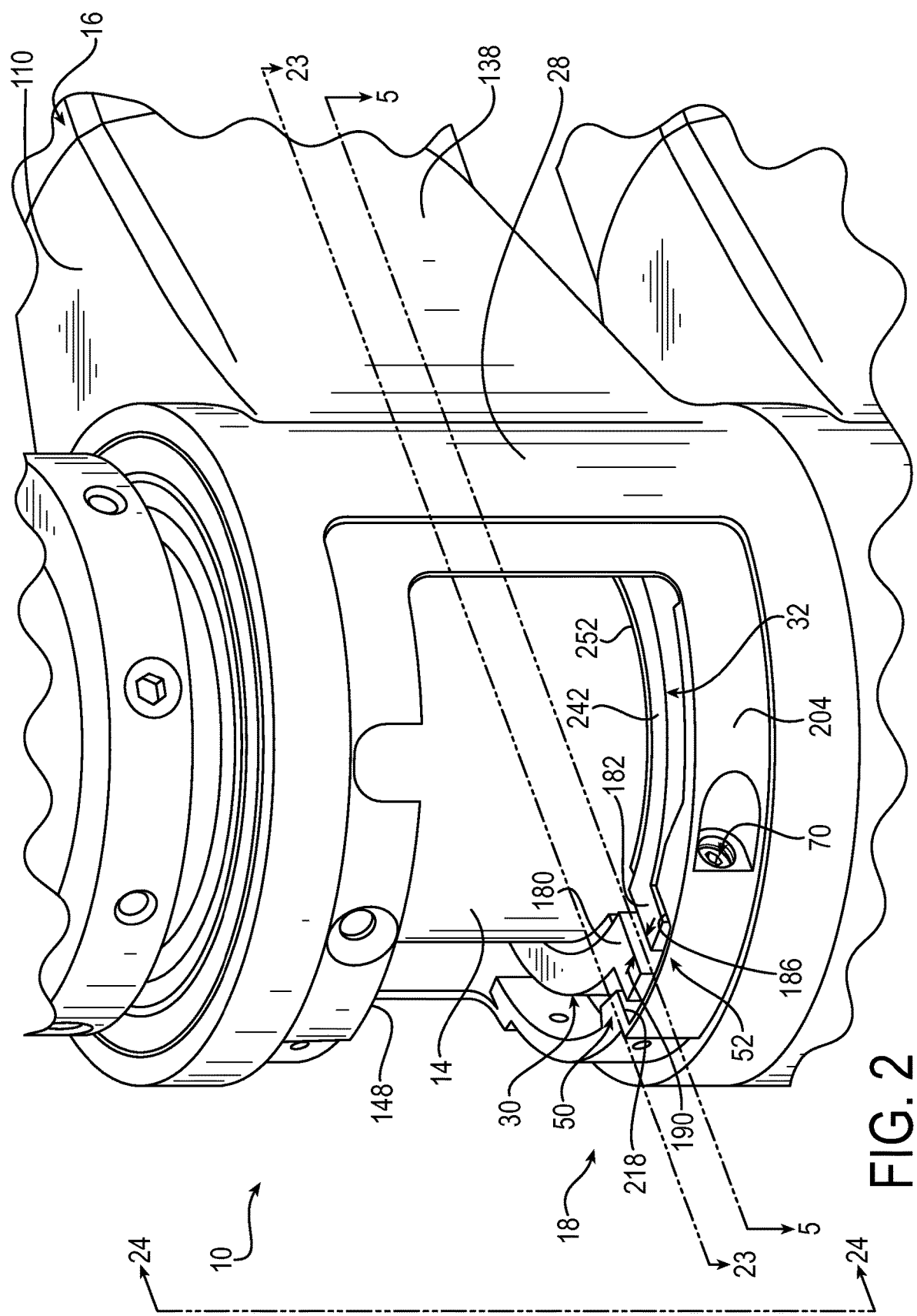
FIG. 2 is a perspective view of a portion of the medical device support system of FIG. 1, showing a pivot location of an extension arm of the system.

Referring to FIG. 1, the illustrative medical device support system 10 is a suspension type carrying support system for use in a hospital examination room, a clinic, a surgery room, an emergency room, among others. The central shaft 14 extends along an axis A-A. The central shaft 14 may be fixed to a ceiling support 80 to remain stationary relative to the ceiling. It will be appreciated, of course, that the medical device support system 10 may have any suitable suspension or carrying structure and that the central shaft 14 may be attached to a ceiling, wall, floor, movable cart, or a combination of the foregoing. The central shaft 14 of the medical device support system 10 has a circular shape in axial cross section and extends vertically downward from the ceiling support 80. A column section 82 surrounds an upper portion of the central shaft 14 and houses upper portions of accessory and service lines such as power cables for surgical lights and other power requirements, control wiring for control electronics, and/or tubing for irrigation, suction, etc. A plurality of extension arms 16, three in the illustrative embodiment, are mounted for rotatable movement to the central shaft 14 and extend laterally outward from the central shaft 14. In the FIG. 1 embodiment, the extension arms 16 extend horizontally, or perpendicularly, relative to the central shaft 14.

Each extension arm 16 is equipped with a support 88 for a medical device 98. The illustrative support 88 is a vertical column 88 extending downward from a distal end 102 of the horizontal extension arm 16. The vertical column 88 may be mounted for rotatable movement to the distal end 102 of the extension arm 16 by means of a bearing, and may be equipped to frictionally engage the distal end 102, for example, by means of a brake assembly 18 in the same manner that the extension arm 16 is rotatably mounted and braked relative to the central shaft 14. In the FIG. 1 embodiment, the medical device 98 comprises a surgical light 98 attached to a bottom end of the vertical column 88. Of course, the medical device support system 10 need not be limited as such and other embodiments are contemplated. For example, the medical device 98 may comprise a patient monitor, a supply console, a camera detector head, a medical instrument, a ventilator system, a suction device, among others. A control console, if provided, may provide controls for navigation of a medical instrument that is either coupled to or remote from the extension arm 16.

The hub 28 is located at the proximal end 110 of the extension arm 16 and is mounted to the central shaft 14 for pivotable movement about the central shaft 14. In the illustrative embodiment, each hub 28 includes upper and lower bearing mounts 114, 116, shown in FIG. 3, that house respective upper and lower pivot bearings mounted to the central shaft 14. Any suitable pivot bearings may be used to facilitate the relative rotational movement between the extension arm 16 and the central shaft 14, including for example ball bearings, sleeve bearings, bushings, rotary joints and/or swivel joints. Each hub 28 provides passages for routing accessory and service lines from the upper column section 82 to the radial extent 138 of the extension arm 16 and/or vice versa. Each hub 28 is also provided with an access opening 148 to enable access to the central shaft 14, the brake assembly 18, and the accessory and service lines.

Figure 3:
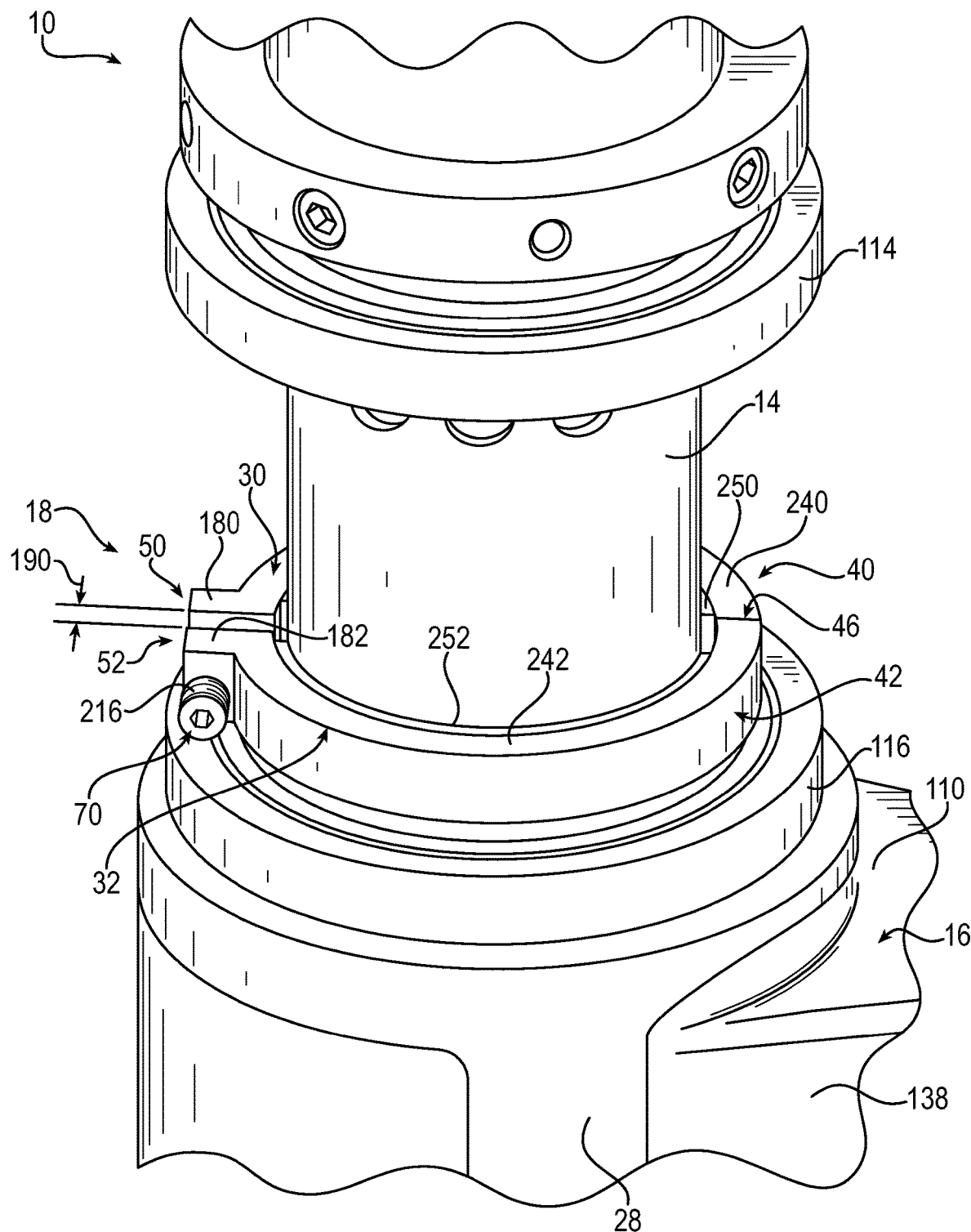
FIG. 3 is a perspective view of a portion of the medical device support system of FIG. 1, showing a pivot location of an extension arm of the system with portions of the extension arm removed to show inner detail.
Figure 4:
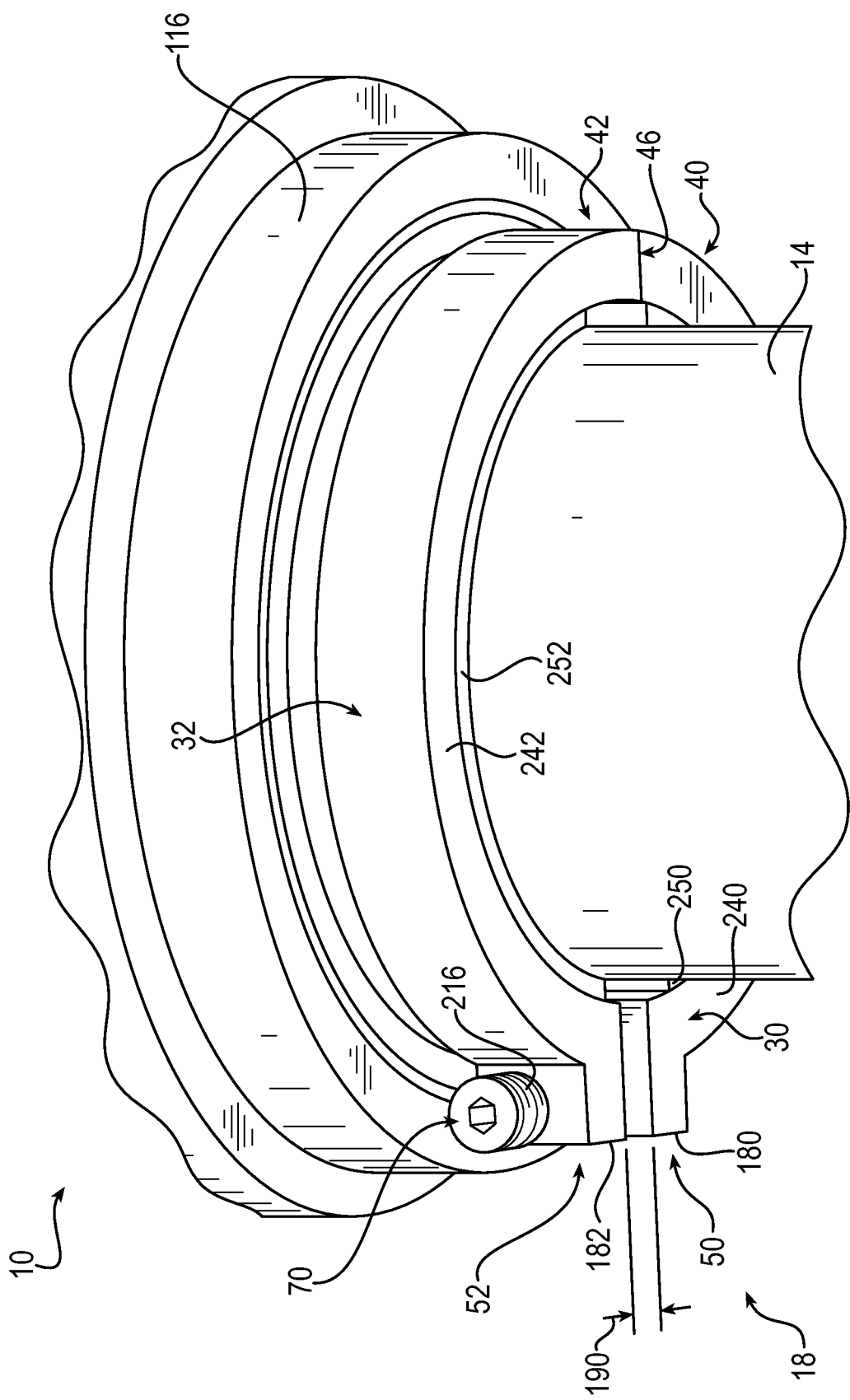
FIG. 4 is a perspective view of a portion of the medical device support system of FIG. 1, showing a pivot location of an extension arm of the system with portions of the extension arm removed to show inner detail.
Figure 5:
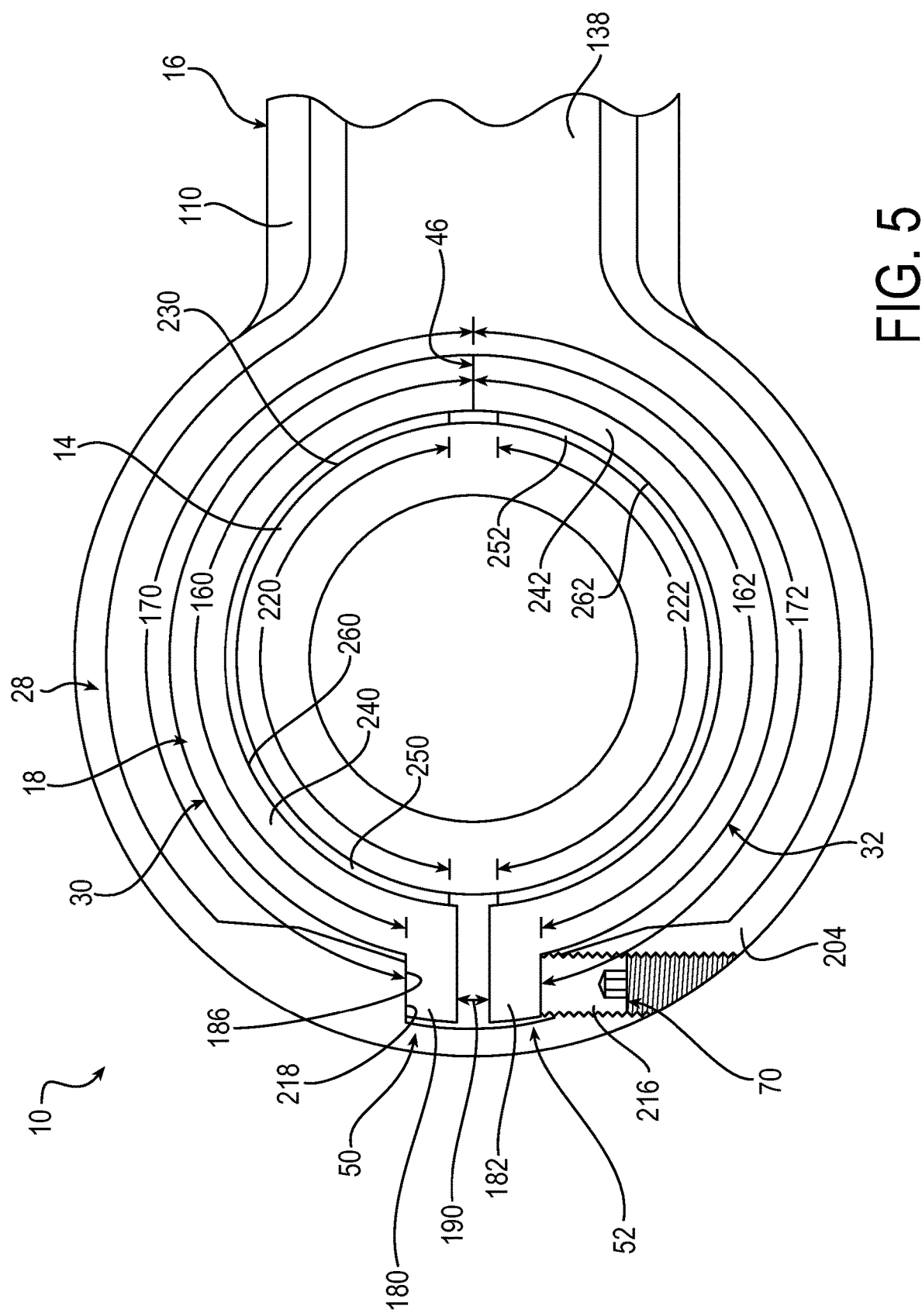
FIG. 5 is a cross-section view of the medical device support system of FIG. 1, as viewed from the plane 5-5 in FIG. 2.

Reference is now made to FIGS. 2-9 which show greater detail of the brake assembly 18. The brake assembly 18 is secured in the hub 28 for rotation with the hub 28. As shown in FIGS. 4 and 5, the brake assembly 18 includes first and second discrete arc shape clamp pieces 30, 32 that are detachably coupled to one another at one end 40, 42 for flexural movement relative to a coupling joint 46 while being free to move at an opposite end 50, 52. In the illustrative embodiment, each of the first and second discrete arc shape clamp pieces 30, 32 of the brake assembly 18 has a circumferential portion 160, 162, a connecting end 40, 42 at one end of the circumferential portion 160, 162, and a free end 50, 52 at an opposite end of the circumferential portion 160, 162. As shown in FIG. 5, the arc shape clamp pieces 30, 32 in their assembled state form a multi-piece split collar or ring wherein the circumferential portions 160, 162 form the ring portion thereof, an interface between the connecting ends 40, 42 forms a first split thereof, and a gap between the free ends 50, 52 forms a second split thereof. The circumferential portions 160, 162 are sized to fit within and radially inward of inner circumferential portions 170, 172 of the hub 28. As shown in FIG. 3, the arc shape clamp pieces 30, 32 may rest by means of gravity directly on the lower bearing mount 116. A retaining snap ring may be mounted in a groove in the central shaft 14 immediately above, or a slight clearance above, the arc shape clamp pieces 30, 32 and/or immediately below, or a slight clearance below, the arc shape clamp pieces 30, 32 to axially retain or guide the arc shape clamp pieces 30, 32 relative to the central shaft 14.

The free ends 50, 52 of the arc shape clamp pieces 30, 32 include tabs 180, 182 that protrude radially outwardly relative to the circumferential portions 160, 162. As shown in FIGS. 2 and 5, the radially protruding tabs 180, 182 fit within a radially protruding notch 186 in the hub 28, which notch 186 is disposed circumferentially between the inner circumferential portions 170, 172 of the hub 28. The tabs 180, 182, when installed in the hub notch 186, circumferentially oppose one another and form a circumferential gap therebetween referred to herein as a deflection compensation split 190.

The brake assembly 18 further includes an actuator 70 that is housed in a wall portion 204 of the hub 28, as shown in FIGS. 2 and 5. The actuator 70 is operative selectively to apply a compressive force to the tabs 180, 182 to urge the first and second arc shape clamp pieces 30, 32 toward one another thereby to impart a frictional braking force to the central shaft 14. In the illustrative embodiment, the actuator 70 comprises a set screw 216 although any type of actuator 70 may be employed that is operative to urge the first and second arc shape clamp pieces 30, 32 toward one another. The set screw 216 is configured to apply a load to the rear of the tab 182. The set screw 216 is threaded into the wall portion 204 of the hub 28 and when threaded inward compresses the tab 182 toward the opposite tab 180. The opposite tab 180 provides resistance to the compressive force applied by the set screw 216 by resting against a wall 218 of the notch 186 in the hub 28.

In operation, tightening the set screw 216 compresses the tabs 180, 182 and thereby narrows the deflection compensation split 190 and flexes the first and second arc shape clamp pieces 30, 32 toward one another relative to the coupling joint 46. Loosening the set screw 216 causes the tabs 180, 182 to separate from one another owing to the resistive force imparted by the notch wall 218 of the hub 28 against the rear of the tab 180, which results in the deflection compensation split 190 expanding and the first and second arc shape clamp pieces 30, 32 unflexing away from one another relative to the coupling joint 46. Thus, the deflection compensation split 190 between the free ends 50, 52 compensates for deflection caused by the application of compressive force on the tabs 180, 182, which creates a tangential frictional force that supplies the braking relative to the central shaft 14. The set screw 216, or actuator 70, is configured to increase and decrease the frictional braking force applied by the brake assembly 18 to the central shaft 14 to respectively increase and decrease the resistance to pivotable movement of the extension arm 16 about the central shaft 14. The actuator 70 and brake assembly 18 are configured to operate in a passive manner, preventing motion of the extension arm 16 relative to the central shaft 14 by means of an "always-on" frictional braking force that can be overcome by a user pushing on the extension arm 16. The amount of frictional resistance can be adjusted as desired by the user by adjusting the actuator 70. The actuator 70 can be used to adjust the frictional resistance as suited for a particular physician and/or on a periodic basis to ensure the previously set frictional resistance still is in place and not loosened over time.

It will be appreciated that a suitable actuator can be employed to generate a lock mode, a frictional resistance mode, and/or a release mode. For example, the actuator can be configured to adjust the brake assembly 18 to generate a braking force, whether by friction or an interengaging mechanism such as a cam lock or piston lock, sufficient to lock the extension arm 16 to the central shaft 14, and/or to generate a frictional braking force that prevents rotation of the extension arm 16 about the central shaft 14 yet enables a user to overcome the resistance by pushing the extension arm 16 about the central shaft 14, and/or to generate a relatively lower or zero frictional braking force sufficient to free or release the extension arm 16 for pivotable movement about the central shaft 14 with relatively less or negligible force by the user. It will further be appreciated that the brake assembly 18 could be adapted for an active braking system, one which provides an active braking functionality that can apply a frictional braking force actively, for example, by means of electromagnetic actuation, pneumatic actuation, or hydraulic actuation.

The multi-piece split collar that is formed by the first and second arc shape clamp pieces 30, 32 is disposed around the central shaft 14 and is configured to contract and expand relative to the central shaft 14 in response to the flexural movement of the first and second arc shape clamp pieces 30, 32 relative to the coupling joint 46. As will be appreciated, as the first and second arc shape clamp pieces 30, 32 of the brake assembly 18 are flexed relative to the coupling joint 46, the circumferential portions 160, 162 and free ends 50, 52 of the arc shape clamp pieces 30, 32 move closer together and farther apart to respectively contract and expand the split collar. As shown in FIG. 5, when the first and second clamp pieces 30, 32 are flexed toward each other to increase the frictional braking force applied to the central shaft 14, the first and second clamp pieces 30, 32 each have an angular range or arc shape contact 220, 222 with the outer periphery 230 of the central shaft 14 of about 165 degrees, or a total of about 330 degrees. Of course, the multi-piece split collar may be formed by more than two discrete arc shape clamp pieces, for example, three or four arc shape clamp pieces, with circumferentially adjacent pieces being detachably coupled together. Further, although the illustrative first and second arc shape clamp pieces 30, 32 are diametrically opposed from one another on opposite sides of the central shaft 14, it will be appreciated that the arc shape clamp pieces 30, 32 may be other than diametrically opposed, for example, where there are more than two arc shape clamp pieces provided. For example, four arc shape clamp pieces may be equally circumferentially disposed about the central shaft 14; that is, each piece may be 90 degrees apart from an adjacent piece.

Figure 6:
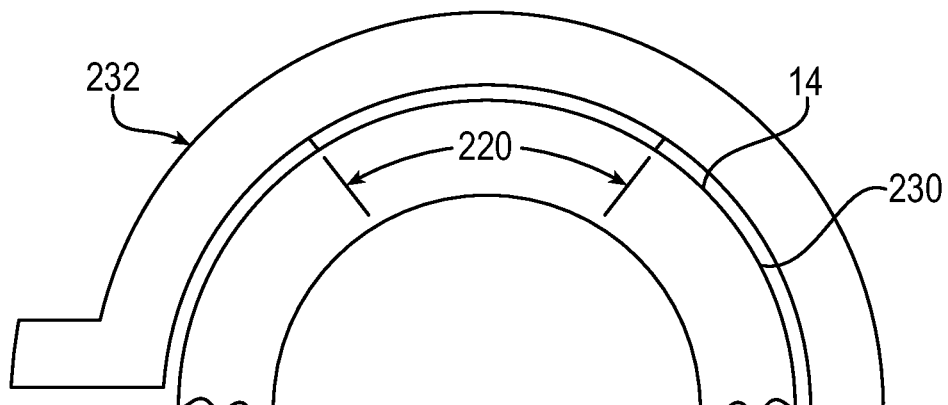
FIG. 6 is a top view of view an arc shape clamp piece of a brake assembly in accordance with an embodiment of the invention.
Figure 7:
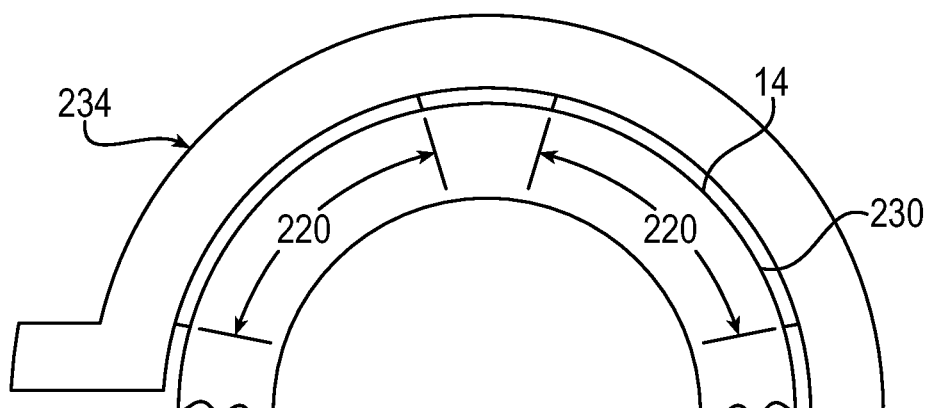
FIG. 7 is a top view of view an arc shape clamp piece of a brake assembly in accordance with another embodiment of the invention.
Figure 8:
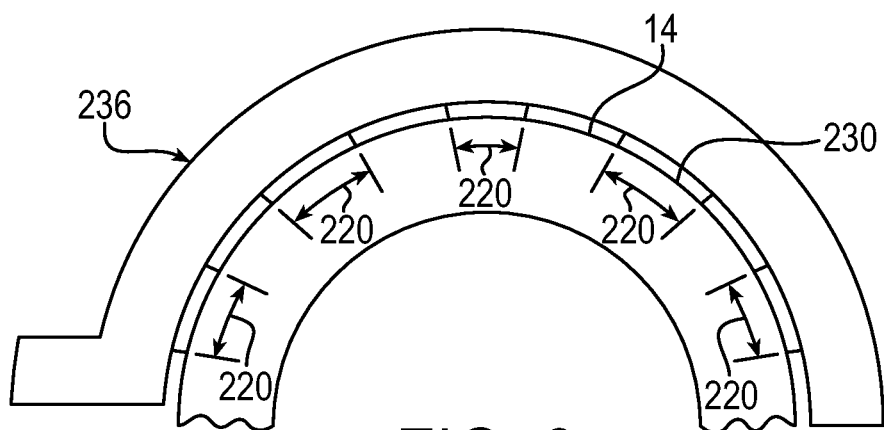
FIG. 8 is a top view of view an arc shape clamp piece of a brake assembly in accordance with another embodiment of the invention.

It will also appreciated that the angular range contact of the arc shape clamp pieces may be other than 165 degrees, and thus other than a total of 330 degrees. For example, FIG. 6 shows an alternate embodiment of an arc shape clamp piece 232 for which the angular range contact with the central shaft 14 is about 30 degrees, thus totaling a 60 degree angular range contact in the case where opposing arc shape clamp pieces 232 have identical geometries. FIG. 7 shows another embodiment in which the arc shape clamp piece 234 has two angular range contacts, one each of about 30 degrees, thus totaling a 120 degree angular range contact in the case where opposing arc shape clamp pieces 234 have identical geometries. FIG. 8 shows yet another embodiment of an arc shape clamp piece 236. Here, the arc shape clamp piece 236 has five angular range contacts, one each of about 15 degrees, thus totaling a 150 degree angular range contact in the case where opposing arc shape clamp pieces 236 have identical geometries. Still other embodiments may have other angular range contacts. It will be understood that opposing arc shape clamp pieces need not have the same angular range contacts, whether in the quantity or size of the arc shape clamp pieces, or the components that form the arc shape clamp pieces.

Figure 9:
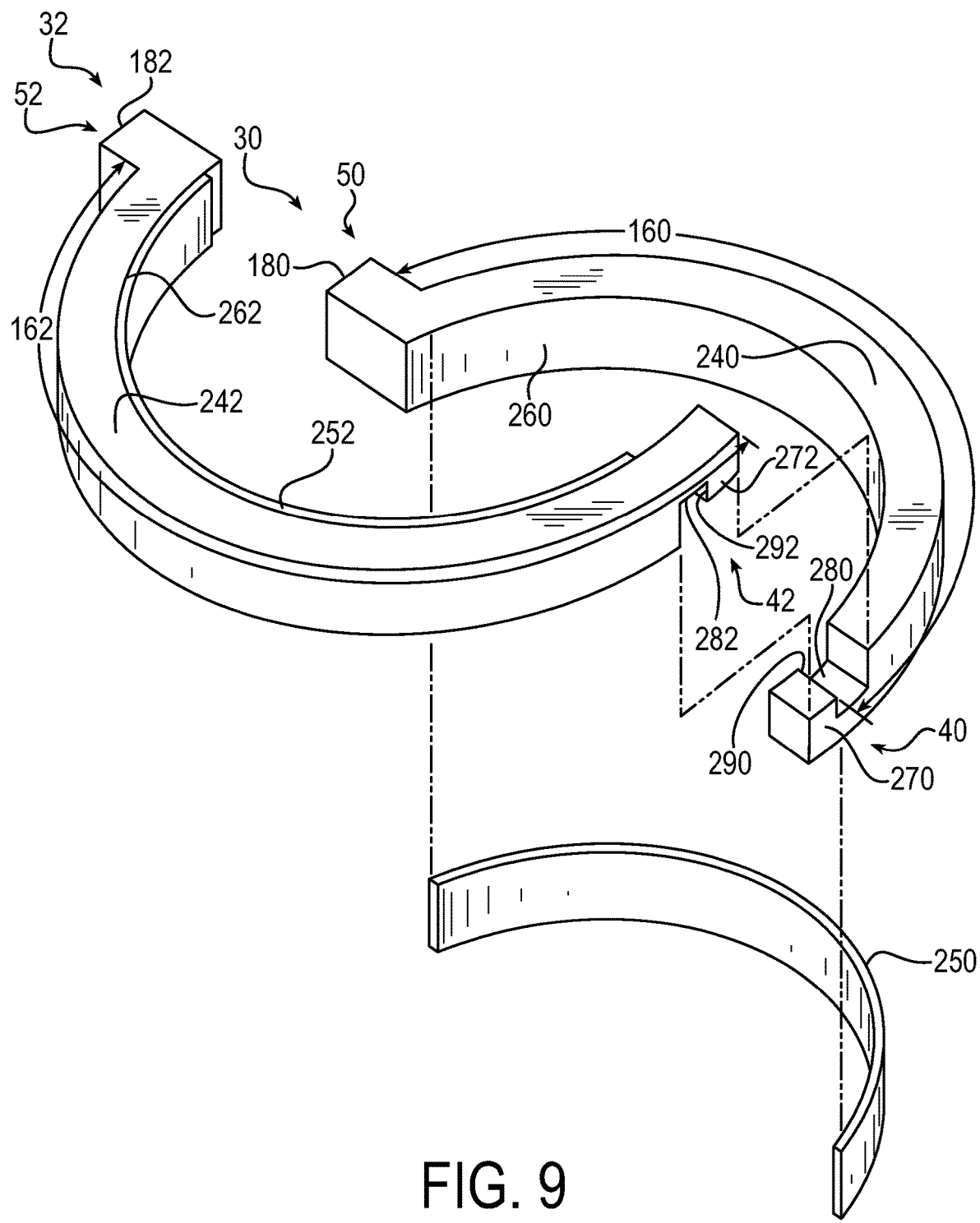
FIG. 9 is an exploded perspective view of first and second arc shape clamp pieces of a brake assembly in accordance with an embodiment of the invention.
Figure 10:
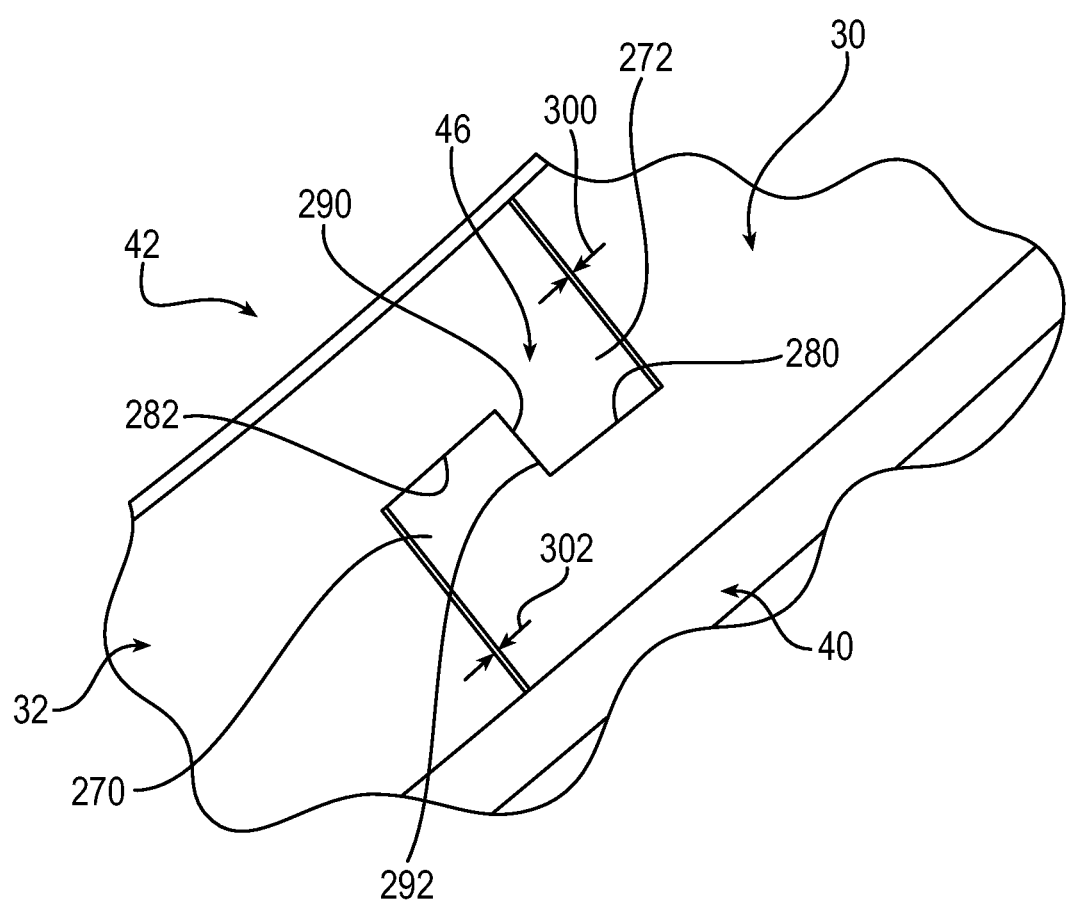
FIG. 10 is a partial side view of a coupling joint of the first and second arc shape clamp pieces of the brake assembly of FIG. 9, showing connecting ends of the pieces detachably coupled to one another.

FIGS. 9 and 10 show greater details of the first and second arc shape clamp pieces 30, 32. The first and second arc shape clamp pieces 30, 32 include an arc shape backing piece 240, 242 and a polymer liner 250, 252 mounted to a radially inner wall 260, 262 of the arc shape backing piece 240, 242, for example by adhesive bonding. In the illustrative embodiment, the arc shape clamp pieces 30, 32 have identical geometries, wherein the arc shape backing pieces 240, 242 have a one part geometry and the polymer liners 250, 252 have a one part geometry. The identical geometries eliminate the need for extra unique component designs. It will be appreciated that the arc shape clamp pieces 30, 32 may have different geometries, or components thereof may have some identical geometries and some different geometries.

The arc shape backing pieces 240, 242 may be made of any suitable materials, for example, metal or metal alloy. The arc shape backing pieces 240, 242 may be made by means of casting, machining, powdered metallurgy and/or metal injection molding. In some applications, the arc shape backing pieces 240, 242 may be made by means of additive manufacturing.

The liners may be formed from any suitable thermoset polymer or thermoplastic polymer. The polymer material may have a low to medium coefficient of friction of about 0.12 to about 0.27, a wear factor no less than about 1.20 E-14 m2/N, a tensile strength of about 4400 to about 12400 psi, a coefficient of linear thermal expansion of about 3.3 to about 7.2 10^-5/F, and a water absorption (50% RH) in a range of about 0.07% to about 0.22%. As one example, the liners may be formed from an unreinforced, semi-crystalline thermoplastic polyester based on polyethylene terephthalate (PET-P), for example, ERTALYTE®. As another example, the liners may be formed from a compression molded ultra high molecular weight polyethylene (UHMW-PE), or an extruded UHMW-PE. As another example, the liners may be formed from an injection molded acetal homopolymer, for example Delrin® 100P. Other suitable polymeric materials include polyolefins (for example, HDPE, LDPE, polypropylene), polyesters (for example, PET, PBT), acetals (for example, Delrin), polyamides (for example, Nylon), fluorinated polymers (for example, PTFE, PFA, FEP, PVDF, ETFE), vinyls (for example, PVC), acrylics (for example, PMMA), polycarbonates, polyimides (for example, PEI), polysulphones (for example, PES), among others, and blends and alloys thereof. The liners may be made by means of injection molding, machining, compression molding and/or extruding. In some applications, the liners may be made by means of additive manufacturing.

The first and second arc shape clamp pieces 30, 32 of the embodiment shown in FIGS. 9 and 10 are detachably coupled to one another by being interlocked to each other at their respective connecting ends 40, 42. As shown in FIG. 10, the connecting ends 40, 42 have respective first and second axially extending tabs 270, 272 and first and second axially extending notches 280, 282, and are configured to be slidable axially and radially relative to one another. The interlocking split allows the first and second clamp pieces 30, 32 to interlock when the compressive loads applied to the tabs 180, 182 create tensile loads at the opposite end connecting ends 40, 42 of the clamp split collar. The arc shape clamp pieces 30, 32 are coupled together by fitting or inserting the first axially extending tab 270 within the second axially extending notch 282, and by fitting or axially inserting the second axially extending tab 272 within the first axially extending notch 280. Once coupled together, the connecting ends 40, 42 form the coupling joint 46 that functions as the joint relative to which the arc shape clamp pieces 30, 32 flex.

During application of a frictional braking force to the central shaft 14, the axially extending tabs 270, 272 circumferentially abut one another at respective opposite facing walls 290, 292 to resist flexural movement of the first and second arc shape clamp pieces 30, 32 toward each other relative to the coupling joint 46. The greater the frictional braking force, the greater is the circumferentially abutting resistance load applied by one facing wall 290 against the opposing facing wall 292.

As shown in FIG. 10, the axially extending notches 280, 282 have an angular width that is wider than the angular width of the axially extending tabs 270, 272. This provides an angular clearance 300, 302 between the tabs 270, 272 and the walls of the notches 280, 282 to facilitate fitting or insertion of the tabs 270, 272 within the respective notches 280, 282, and thus easy assembly of the interlocking split that forms the coupling joint 46. The radially protruding tabs 180, 182 are then positioned in the hub notch 186. In one form, in the initial assembly of the interlocking split and insertion of the tabs 180, 182 in the hub notch 186, the axially extending tabs 270, 272 may be circumferentially separate from one another such that the arc shape clamp pieces 30, 32 are in an unflexed or relaxed state. In another form, in the initial assembly of the interlocking split and insertion of the tabs 180, 182 in the hub notch 186, the axially extending tabs 270, 272 may be in circumferentially abutting relation at the opposite facing walls 290, 292 such that the arc shape clamp pieces 30, 32 are in a slightly flexed state. In any event, the actuator 70 may then be used to urge the first and second arc shape clamp pieces 30, 32 toward one another thereby to impart the desired frictional braking force to the central shaft 14. When the first and second arc shape clamp pieces 30, 32 are urged toward each other to apply or adjust the frictional braking force to the central shaft 14, the axially extending tabs 270, 272 and thus the arc shape clamp pieces 30, 32 engage one another and form the coupling joint 46 relative to which the arc shape clamp pieces 30, 32 flex in applying the frictional braking force to the shaft 14, as above described. Similarly, when the actuator 70 is backed off, the first and second arc shape clamp pieces 30, 32 flex away from each other to decrease the frictional braking force applied to the central shaft 14.

FIG. 9 shows the axially extending notches 280, 282 are open at their radially opposite ends. This enables radial movement of the axially extending tabs 270, 272 such that when the first and second arc shape clamp pieces 30, 32 are urged toward each other to apply a frictional braking force to the central shaft 14, the axially extending tabs 270, 272 and thus the arc shape clamp pieces 30, 32 shift radially relative to one another and, being in circumferentially abutting relation, engage one another and form the coupling joint 46 relative to which the arc shape clamp pieces 30, 32 flex in applying the frictional braking force to the shaft 14, as above described. Similarly, when the first and second arc shape clamp pieces 30, 32 are flexed away from each other to decrease the frictional braking force applied to the central shaft 14, the axially extending tabs 270, 272 and thus the arc shape clamp pieces 30, 32 move radially relative to one another as they unflex.

As will be appreciated, the first and second arc shape clamp pieces 30, 32 can "float" relative to each other axially, circumferentially, and radially. As such, when the actuator 70 urges the radially protruding tabs 180, 182 together to urge the arc shape clamp pieces 30, 32 closer together or opens the deflection compensation split 190 to allow the arc shape claim pieces 30, 32 to move apart, the arc shape clamp pieces 30, 32 are able to shift to a position that is most centered and aligned with respect to the central shaft 14. Thus, the floating capability enables the multi-piece split collar that is formed by the arc shape clamp pieces 30, 32 to be self-centering and self-aligning relative to the central shaft 14. This also allows for a built-in concentricity clearance between the hub 28 and the brake assembly 18, particularly over repeated angular adjustments of the extension arm 16 relative to the central shaft 14.

It will be appreciated that the connecting ends 40, 42 of the first and second arc shape clamp pieces 30, 32 need not be limited to the detachable coupling configuration shown in FIGS. 9 and 10, and other embodiments are contemplated. The first and second arc shape clamp pieces 30, 32 may include any type of first and second axially extending protrusions that circumferentially abut one another to resist flexural movement of the first and second arc shape clamp pieces 30, 32 toward each other relative to the coupling joint 46.

Figure 11:
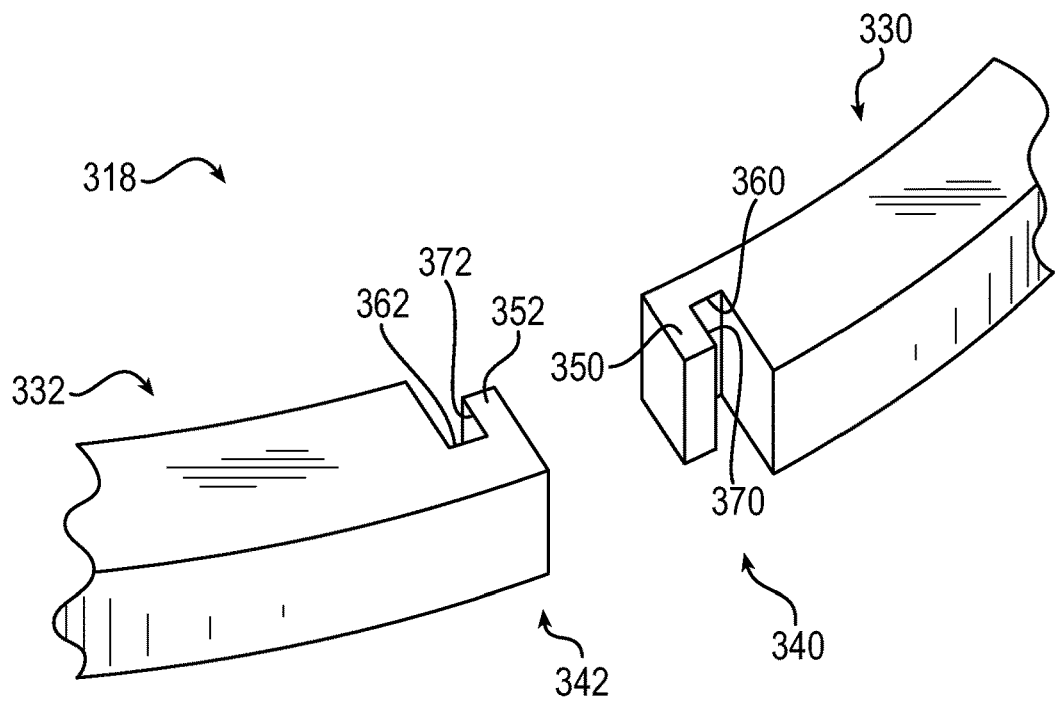
FIG. 11 is a perspective view of connecting ends of first and second arc shape clamp pieces of a brake assembly in accordance with an embodiment of the invention.

FIG. 11, for example, shows first and second arc shape clamp pieces 330, 332 in which the connecting ends 340, 342 have respective first and second axially extending tabs 350, 352 and first and second axially extending notches 360, 362 that are configured to be slidable axially and radially relative to one another. As will be appreciated, the chief difference between the FIG. 9 and FIG. 11 embodiments is that the tabs 270, 272 project axially from the circumferential portions 160, 162 in FIG. 9, and the tabs 340, 342 project radially from the circumferential portions 160, 162 in FIG. 11. The arc shape clamp pieces 330, 332 are coupled together by fitting or inserting the first axially extending tab 350 within the second axially extending notch 362, and by fitting or axially inserting the second axially extending tab 352 within the first axially extending notch 360. Once coupled together, the connecting ends 340, 342 form the aforementioned coupling joint 46 that functions as the joint relative to which the arc shape clamp pieces 330, 332 flex. During application of a frictional braking force to the central shaft 14, the axially extending tabs 350, 352 circumferentially abut one another at respective opposite facing walls 370, 372 to resist flexural movement of the first and second arc shape clamp pieces 330, 332 toward each other relative to the coupling joint 46. The greater the frictional braking force, the greater is the circumferentially abutting resistance load applied by one facing wall 370 against the opposing facing wall 372.

The axially extending notches 360, 362 have an angular width that is wider than the angular width of the axially extending tabs 350, 352. This provides an angular clearance between the tabs 350, 352 and the walls of the notches 360, 362 to facilitate fitting or insertion of the tabs 350, 352 within the respective notches 360, 362, and thus easy assembly of the interlocking split that forms the coupling joint 46. The radially protruding tabs 180, 182 are then positioned in the hub notch 186. In one form, in the initial assembly of the interlocking split and insertion of the tabs 180, 182 in the hub notch 186, the axially extending tabs 350, 352 may be circumferentially separate from one another such that the arc shape clamp pieces 330, 332 are in an unflexed or relaxed state. In another form, in the initial assembly of the interlocking split and insertion of the tabs 180, 182 in the hub notch 186, the axially extending tabs 350, 352 may be in circumferentially abutting relation at the opposite facing walls 370, 372 such that the arc shape clamp pieces 330, 332 are in a slightly flexed state. In any event, the actuator 70 may then be used to urge the first and second arc shape clamp pieces 330, 332 toward one another thereby to impart the desired frictional braking force to the central shaft 14. When the first and second arc shape clamp pieces 330, 332 are urged toward each other to apply the frictional braking force to the central shaft 14, the axially extending tabs 350, 352 and thus the arc shape clamp pieces 330, 332 engage one another and form the coupling joint 46 relative to which the arc shape clamp pieces 330, 332 flex in applying the frictional braking force to the shaft 14, as above described. Similarly, when the actuator 70 is backed off, the first and second arc shape clamp pieces 330, 332 flex away from each other to decrease the frictional braking force applied to the central shaft 14.

Further, the axially extending notches 360, 362 are open at their radially opposite ends. This enables radial movement of the axially extending tabs 350, 352 such that when the first and second arc shape clamp pieces 330, 332 are urged toward each other to apply a frictional braking force to the central shaft 14, the axially extending tabs 350, 352 and thus the arc shape clamp pieces 330, 332 shift radially relative to one another and, being in circumferentially abutting relation, engage one another and form the coupling joint 46 relative to which the arc shape clamp pieces 330, 332 flex in applying the frictional braking force to the shaft 14, as above described. Similarly, when the first and second arc shape clamp pieces 330, 332 are flexed away from each other to decrease the frictional braking force applied to the central shaft 14, the axially extending tabs 350, 352 and thus the arc shape clamp pieces 330, 332 move radially relative to one another as they unflex.

Figure 12:
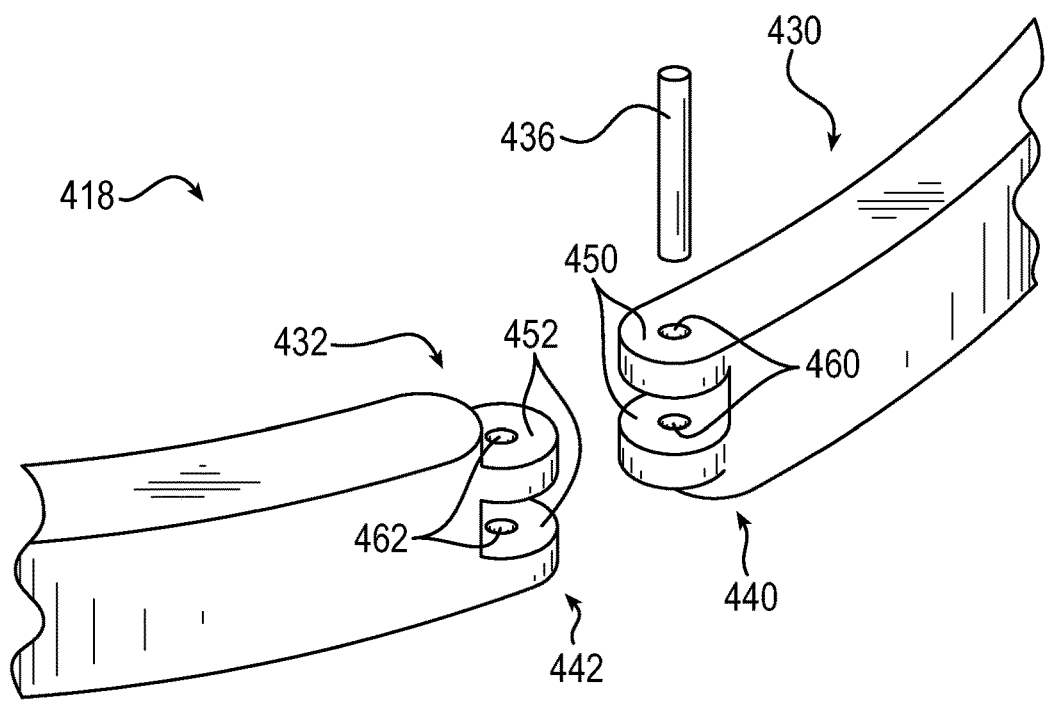
FIG. 12 is a perspective view of connecting ends of first and second arc shape clamp pieces of a brake assembly in accordance with an embodiment of the invention.

FIG. 12 shows another embodiment. Here, first and second arc shape clamp pieces 430, 432 are detachably coupled to one another by a hinge 436, a pin 436 in the illustrative embodiment, at the respective connecting ends 440, 442. The arc shape clamp pieces 430, 432 are coupled together by interlocking hinge prongs 450, 452 and sliding the pin 436 axially into holes 460, 462 in the respective prongs 450, 452. Once coupled together, the connecting ends 440, 442 form the coupling joint 46 that functions as the joint relative to which the arc shape clamp pieces 430, 432 flex. During application of a frictional braking force to the central shaft 14, the pin 436 holds the hinge prongs 450, 452 circumferentially together to resist flexural movement of the first and second arc shape clamp pieces 430, 432 toward each other relative to the coupling joint 46. The greater the frictional braking force, the greater is the resistance load by the pin 436 against the opposing hinge prongs 450, 452. As will be appreciated, axial, circumferential and radial clearances can be built into the holes 460, 462 to enable respective axial, circumferential and radial shifting between the arc shape clamp pieces 430, 432, in substantially the same manner as the embodiments of FIG. 9 and FIG. 11.

Figure 13:
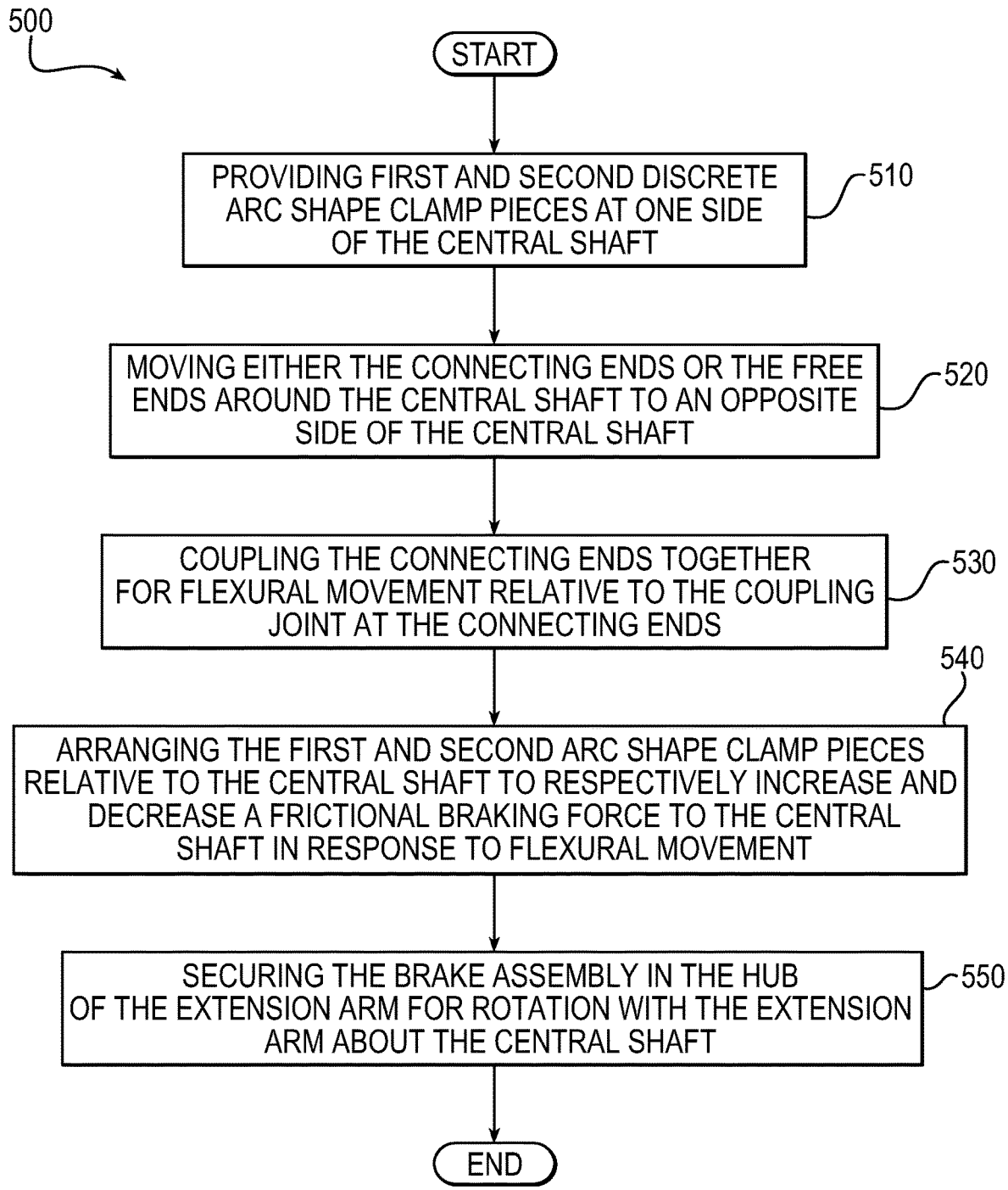
FIG. 13 shows a flowchart of a method of installing a brake assembly in a medical device support system in accordance with an embodiment of the invention.

Referring now to FIG. 13, there is shown a flowchart 500 of a method of installing a brake assembly in a medical device support system, such as the brake assembly 18 in the medical device support system 10 of FIG. 1. At step 510, the first and second discrete arc shape clamp pieces 30, 32 of the brake assembly 18 are provided at one side of the central shaft 14, for example, in a position radially outward of the central shaft 14. This may be in a health treatment room such as a surgery room, for example, where the central shaft 14 is made accessible for example by an access opening 148 as shown in FIG. 2. At step 520, either the connecting ends 40, 42 or the free ends 50, 52 of the first and second discrete arc shape clamp pieces 30, 32 are moved around the central shaft 14 to an opposite side of the central shaft 14 so that the connecting ends 40, 42 and free ends 50, 52 are situated at opposite sides of the central shaft 14. At step 530, the connecting ends 40, 42 are coupled together for flexural movement relative to the coupling joint 46 at the connecting ends 40, 42 and for free movement at the free ends 50, 52. At step 540, the first and second arc shape clamp pieces 30, 32 are arranged relative to the central shaft 14 to respectively increase and decrease a frictional braking force to the central shaft 14 in response to flexural movement of the first and second arc shape clamp pieces 30, 32 relative to the coupling joint 46. At step 550, the brake assembly 18 is secured in the hub 128 of the extension arm 16 for rotation with the extension arm 16 about the central shaft 14.

The arranging step can include arranging the first and second arc shape clamp pieces 30, 32 to form a multi-piece split collar around the central shaft 14 that is configured to contract and expand relative to the central shaft 14 in response to flexural movement of the first and second arc shape clamp pieces 30, 32 relative to the coupling joint 46. The multi-piece collar can be any number of clamp pieces and need not be limited to two clamp pieces. The coupling step can include interlocking the connecting ends 40, 42 of the first and second arc shape clamp pieces 30, 32. The coupling step can include sliding the first and second arc shape clamp pieces 30, 32 axially relative to one another, as in the embodiments of FIGS. 9 and 11. The coupling step can include hingedly connecting the connecting ends 340, 342 of the first and second arc shape clamp pieces 430, 432, as in the embodiment of FIG. 12. The method can further include mounting a retaining snap ring in a groove in the central shaft 14 to axially retain the first and second arc shape clamp pieces onto the central shaft 14.

Figure 14:
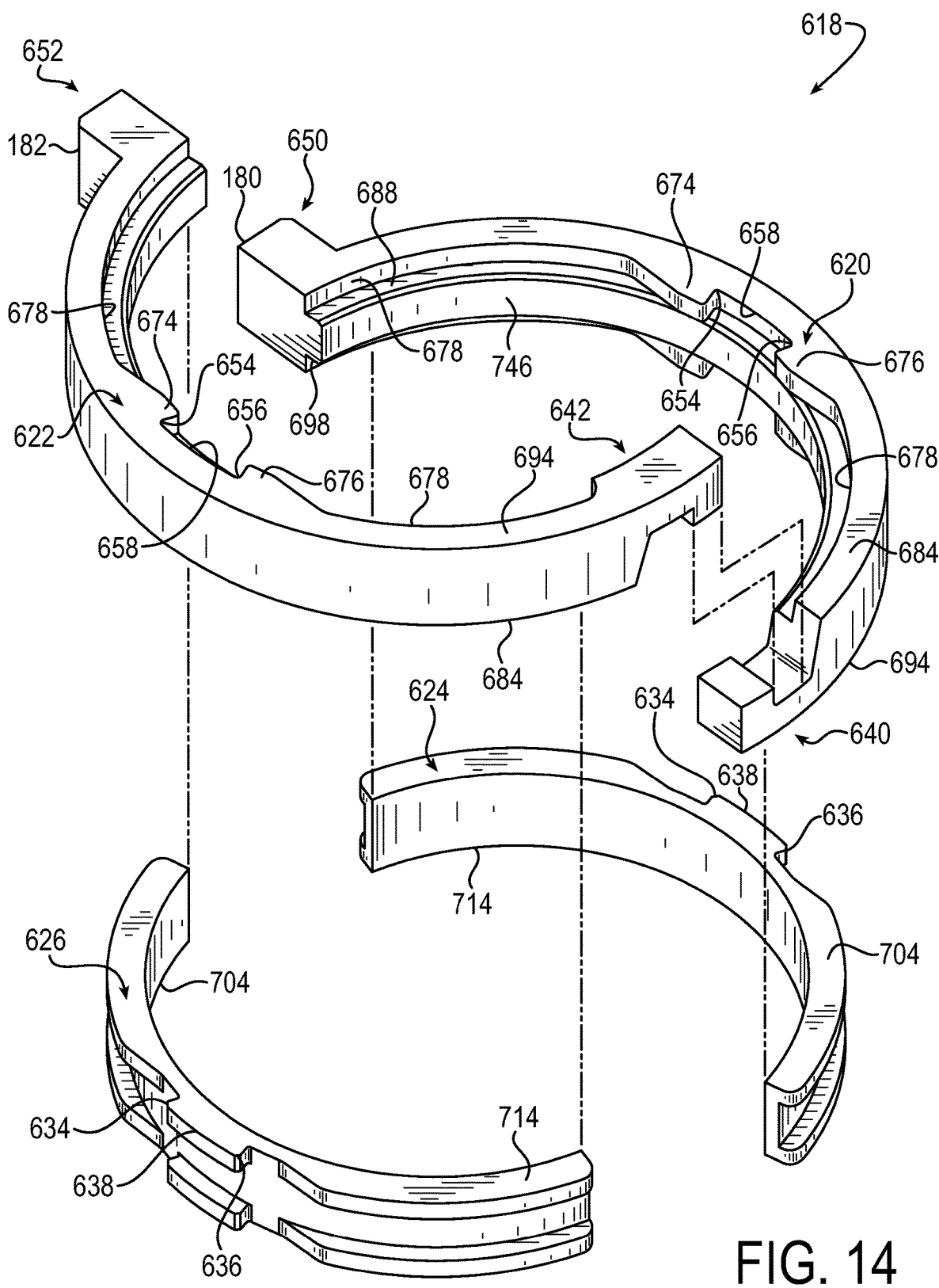
FIG. 14 is an exploded perspective view of first and second backing portions and first and second liners of a brake assembly in accordance with an embodiment of the invention.
Figure 21:
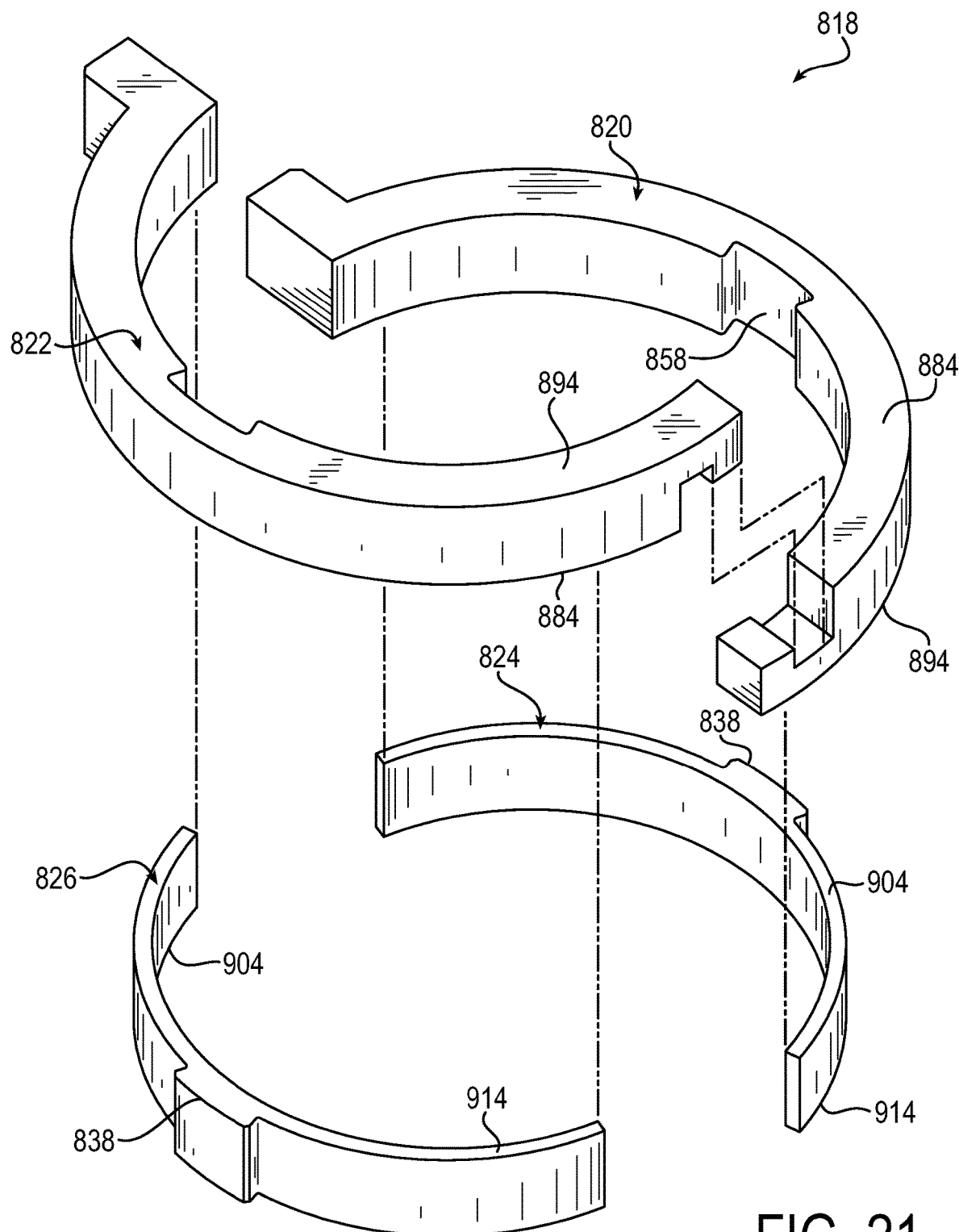
FIG. 21 is an exploded perspective view of first and second backing portions and first and second liners of a brake assembly in accordance with an embodiment of the invention.

FIGS. 14 and 21 illustrate respective brake assemblies 618, 818 according to other embodiments of the invention. The brake assemblies 618, 818 are in many respects similar to the above-referenced FIG. 9 brake assembly 18, and consequently the same reference numerals but indexed by 600, 800 respectively, are used to denote structures corresponding to similar structures in the FIG. 9 brake assembly 18. In addition, the foregoing description of the FIG. 9 brake assembly 18, including its configuration and function relative to other components of the medical device support system 10, is equally applicable to the brake assemblies 618, 818 in FIGS. 14 and 21. Further, the foregoing description of the coupling joints 46 and connecting ends 40, 42, 340, 342, 440, 442 of the brake assemblies 18, 318, 418 of FIGS. 9, 11 and 12 is equally applicable to the brake assemblies 618, 818 in FIGS. 14 and 21. Thus, any of the coupling joints in FIGS. 9, 11 and 12 can be used in connection with the brake assemblies 618, 818 of FIGS. 14 and 21. Moreover, it will be appreciated upon reading and understanding the specification that aspects of the brake assemblies 18, 318, 418, 618, 818 may be substituted for one another or used in conjunction with one another where applicable. Thus, for example, it will be appreciated that any of the snap-fit connections of the brake assemblies 618, 818 of FIGS. 14 and 21 described hereafter can be used in connection with the brake assemblies 18, 318, 418 of FIGS. 9, 11 and 12.

The brake assembly 618 incorporates a dovetail type snap-fit connection and is shown in greater detail in FIGS. 14-18. The brake assembly 618 is secured in the hub 28 of the extension arm 16 for rotation therewith (FIG. 1). The brake assembly 618 includes first and second backing portions 620, 622 and first and second liners 624, 626 supported by the backing portions 620, 622. The liners 624, 626 are supported by the backing portions 620, 622 by being snap-fitted to the backing portions 620, 622. The actuator 70 (FIGS. 2-5) is configured to flex the first and second backing portions 620, 622 to urge the first and second liners 624, 626 toward and away from each other to respectively increase and decrease a frictional braking force to the central shaft 14 (FIG. 3), which, in turn, respectively increases and decreases the resistance to pivotable movement of the extension arm 16 about the central shaft 14. As will be described in greater detail in the following, the snap-fit connection enables the first and second liners 624, 626 to be easily assembled to, and removed from, the backing portions 620, 622, and therefore simplifies and adds efficiency to the factory assembly and field service of the medical device support system 10.

The backing portions 620, 622 and liners 624, 626 may have an arc shape, similar to the arc shape backing pieces 240, 242 and arc shape liners 250, 252 of the FIG. 9 brake assembly 18. The backing portions 620, 622 and liners 624, 626 may form a split collar around the central shaft 14 that is configured to contract and expand relative to the central shaft 14 in response to flexural movement of the first and second backing portions 620, 622. In one form, the split collar may be in the form of a C-shape clamp in which, for example, the first and second backing portions 620, 622 are of a unitary construction, or a monolithic clamp, i.e. not separate pieces. In another form, the split collar may be in the form of a multi-piece split collar in which, for example, the first and second backing portions 620, 622 and the first and second liners 624, 626 are discrete pieces, i.e. first and second backing pieces and the first and second liner pieces, similar to the arc shape backing pieces 240, 242 and arc shape liners 250, 252 of the FIG. 9 brake assembly 18. Other embodiments are also contemplated. For example, one backing portion may be configured with a snap-fit liner while the other backing portion is configured with a glued liner. As another example, the first and second liners 624, 626 may be of unitary construction, i.e. not separate pieces, for example by being injection molded with a flexible strip located circumferentially between circumferentially adjacent ends of the first and second liners 624, 626.

Figure 15:
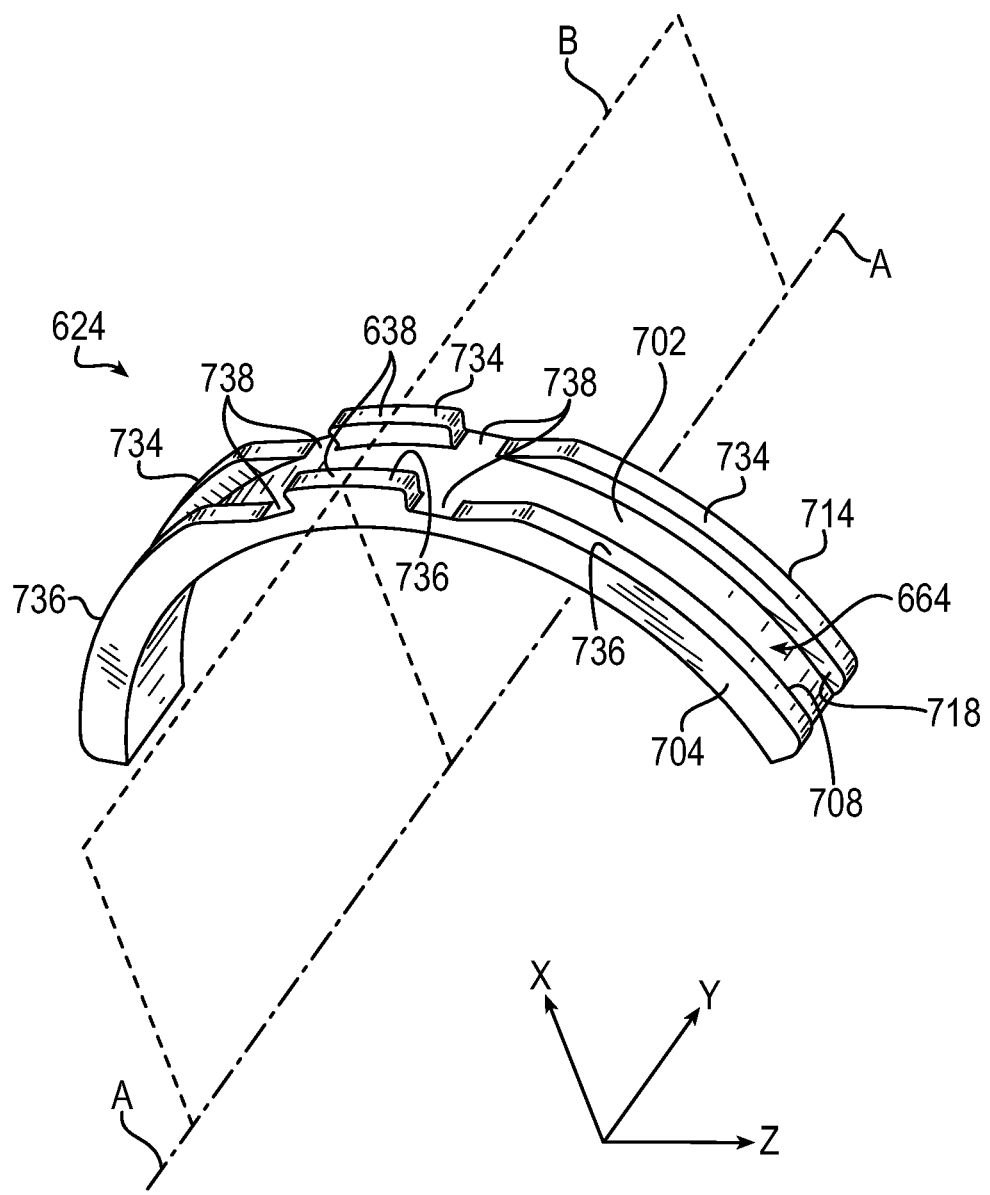
FIG. 15 is a perspective view of a liner of the FIG. 14 brake assembly.

The first and second backing portions 620, 622 may have a one part geometry, i.e. an identical geometry. The first and second liners 624, 626 may also or alternatively have a one part geometry, i.e. an identical geometry. As shown in FIG. 15, the liners 624, 626 may also be symmetrical about a radial plane B passing through the liner 624, 626, in the illustrative embodiment passing through the angular center of the arc shape of the liner 624, 626. The identical geometries eliminate the need for extra unique component designs. The symmetry in the liners 624, 626 simplifies assembly and field service. It will be appreciated that the backing portions 620, 622 may have different geometries and the liners 624, 626 may have different geometries, or components thereof may have some identical geometries and some different geometries. It will further be appreciated that the liners 624, 626 need not be symmetrical about a radial plane and may instead be asymmetrical about a radial plane.

In operation, as the actuator 70 flexes the first and second liners 624, 626 of the brake assembly 618 toward each other to increase the frictional braking force applied to the central shaft 14, the first and second liners 624, 626 each have an angular range contact with the outer periphery 230 of the central shaft 14 of about 165 degrees, or a total of about 330 degrees, similar to the angular range contact 220, 222 of the liners 250, 252 of the brake assembly 18 shown in FIG. 5. The frictional braking force maintains the extension arm 16 in the desired angular position relative to the central shaft 14, as earlier described. Of course, the brake assembly 618 may include more than two liners 624, 626, for example, three or four liners, with each liner being snap-fitted to one of the backing portions 620, 622. Further, it will be appreciated that the angular range contact of the liners 624, 626 may be other than 165 degrees, and thus other than a total of 330 degrees. Further, although the illustrative first and second liners 624, 626 are diametrically opposed from one another on opposite sides of the central shaft 14, it will be appreciated that the liners 624, 626 may be other than diametrically opposed, particularly where there are more than two liners 624, 626 provided. For example, four liners may be equally circumferentially disposed about the central shaft 14; that is, each liner may be 90 degrees apart from an adjacent liner.

The first and second backing portions 620, 622 may be made of a metal or metal alloy, similar to the arc shape backing pieces 240, 242 of the FIG. 9 brake assembly 18. The liners 624, 626 may be made of any suitable polymer material, such as the polymer materials identified above with respect to the liners 250, 252.

The first and second liners 624, 626 include at least one protruding part 634, 636, four total in the illustrative embodiment, and the first and second backing portions 620, 622 have at least one undercut 654, 656, also four total in the illustrative embodiment. The liners 624, 626 are snap-fitted to the respective first and second backing portions 620, 622 by the undercuts 654, 656 receiving the respective protruding parts 634, 636. In the FIG. 14 brake assembly 618, the protruding parts 634, 636 form a radially protruding dovetail 638 and the undercuts 654, 656 form a radially protruding receptacle 658 into which the dovetail 638 seats when the liners 624, 626 are snap-fitted to the backing portions 620, 622. In particular, the liners 624, 626 have a pair of the radially protruding dovetails 638, which are axially spaced apart by a later described groove 664 in the liner 624, 626. Similarly, the backing portions 620, 622 have a pair of the radially protruding receptacles 658, which likewise are axially spaced apart about the same width as the dovetails 638 by a later described tongue 668. As will be appreciated, any quantity of snap-fit features may be suitable for a particular application, the FIG. 14 pair of dovetails 638 and pair of receptacles 658 being only one example. Thus, a brake assembly may have a backing portion with a single radially protruding receptacle and a liner with a single radially protruding dovetail.

The protruding parts 634, 636 of the dovetails 638 are configured to deflect briefly during a fitting operation and subsequently catch in a respective undercut 654, 656 of the mating receptacles 658 of the first and second backing portions 620, 622. As will be appreciated, any suitable fitting operation may be employed. In one form, for example, the fitting operation may include deflecting both protruding parts 634, 636 of the dovetails 638 before catching in the respective undercuts 654, 656 of the receptacles 658. In another form, the fitting operation may include inserting one of the protruding parts 634 of the dovetails 638 partially into the respective undercut 654 of the receptacles 658 and deflecting the other of the protruding parts 636 before catching in the respective undercut 656.

Figure 16:
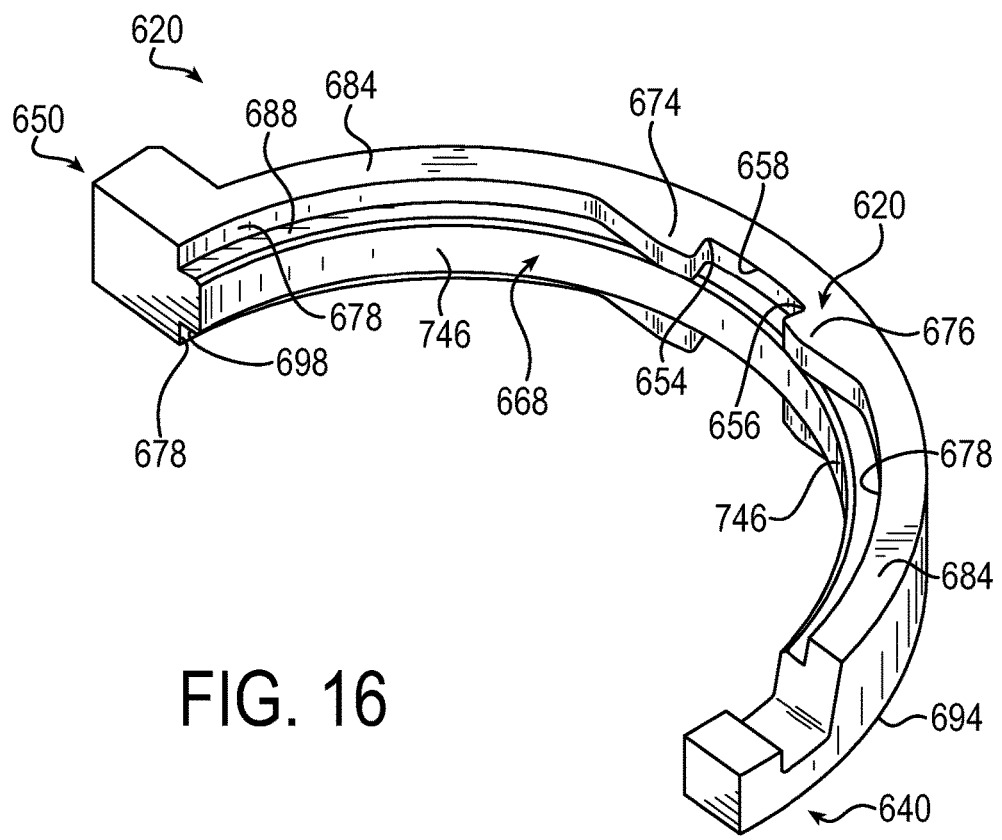
FIG. 16 is a perspective view of a backing portion of the FIG. 14 brake assembly.

FIGS. 15 and 16 show greater detail of a radially protruding dovetail 638 and a radially protruding receptacle 658. On circumferentially opposite skies of the radially protruding receptacle 658 are a pair of bosses 674, 676 that project radially inwardly from a radially inwardly facing wall 678 of the backing portions 620, 622. The bosses 674, 676 also project circumferentially toward one another the further they project radially inwardly, thus forming the respective undercuts 654, 656. As shown in FIG. 16, the undercuts 654, 656 of one of the pair of receptacles 658 extend axially from an axial face 684 to a tongue edge wall 688, and the undercuts 654, 656 of the other of the pair of receptacles 658 extend axially from an opposite facing axial face 694 to an opposite facing tongue wall 698. In the illustrative embodiment, the undercuts 654, 656 are axially parallel to one another. In a complementary manner, on circumferentially opposite sides of the radially protruding dovetail 638 are the pair of protruding parts 634, 636. Thus, as shown in FIG. 15, the protruding parts 634, 636 project radially outwardly from a radially outwardly facing wall 702 of the liners 624, 626, and project circumferentially away from one another the further they project radially outwardly, such that the shape of the protruding parts 634, 636 is complementary to the shape of the undercuts 654, 656 provided by the bosses 674, 676. The protruding parts 634, 636 of one of the pair of dovetails 638 extend axially from an axial face 704 to a groove edge wall 708, and the protruding parts 634, 636 of the other of the pair of dovetails 638 extend axially from an opposite facing axial face 714 to an opposite facing groove edge wall 718. In the illustrative embodiment, the protruding parts 634, 636 are axially parallel to one another.

Figure 17:
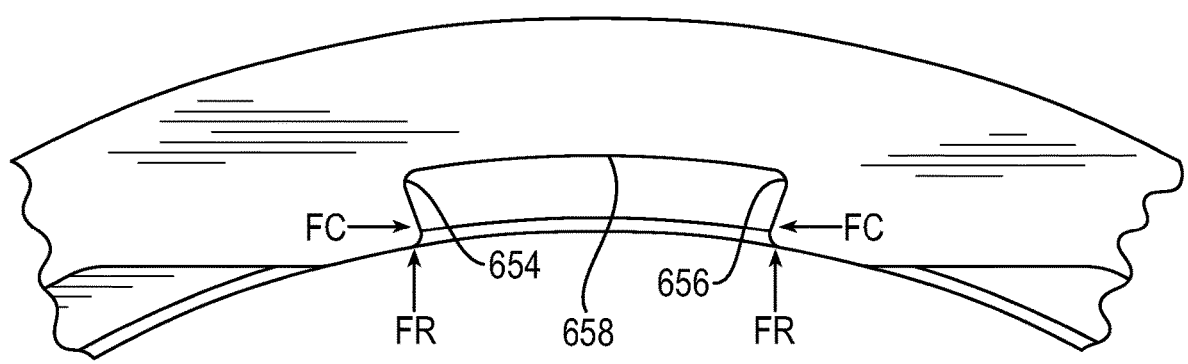
FIG. 17 is a partial side view of a receptacle of the first and second backing portions of the brake assembly of FIG. 14, showing resisting forces.

It will be appreciated that in the FIG. 14 configuration the snap-fit connection between the first and second liners 624, 626 and the first and second backing portions 620, 622 resists radial and circumferential movement of the liners 624, 626 relative to the backing portions 620, 626. In the snap-fitted state, the protruding parts 634, 636 seat within the undercuts 654, 656. As shown in FIG. 17, the bosses 674, 676 exert a resisting force, force FC, that resists circumferential movement of the liners 624, 626 relative to the backing portions 674, 676, as may be exhibited for example by torsional loading on the inside radius of the liners 624, 626 when preventing or resisting pivotable movement of the extension arm 16 about the central shaft 14. Similarly, the bosses 674, 676 exert a resisting force, force FR, that resists radially inward movement of the liners 624, 626 relative to the backing portions 674, 676, as may be exhibited for example by the backing portions 620, 622 flexing away from each other to urge the liners 624, 626 apart to decrease the frictional braking force applied by the brake assembly 618 to the central shaft 14.

The snap-fit mechanism need not be limited to the configuration shown in FIG. 14, and other embodiments are contemplated. For example, the snap-fit mechanism need not take the form of a radially protruding dovetail 638 and radially protruding receptacle 658, and may instead take the form of a cantilever snap-fit joint or an annular snap fit joint. The protruding parts 634, 636 can be in the form of a stud, hook, bead, among others, and the undercuts 654, 656 may be in the form of an edge opening, a notch, a flange, a depression, among others. Further, in one form the backing portions 620, 622 may include the protruding part(s) while the liners 624, 626 include the undercut(s). In another form, the backing portions 620, 622 may include both a protruding part(s) and an undercut(s) that fit to a respective undercut(s) and protruding part(s) in the liners 624, 626.

Still referring to FIGS. 14-16, the first and second backing portions 620, 622 and the first and second liners 624, 626 also include a circumferential tongue and groove connection 722. As shown in FIG. 15, the liners 624, 626 have a circumferentially extending groove 664 defined at axially opposite sides by a pair of flanges 734, 736. The flanges 734, 736 project radially inwardly from the radially outwardly facing wall 702 of the liners 624, 626. The flanges 734, 736 are interrupted along the circumference or more specifically the arc portion by recesses 738 to accommodate the bosses 674, 676 of the backing portions 620, 622. As such, a circumferentially intermediate portion of the flanges 734, 736 forms the pair of radially protruding dovetails 638. As shown in FIG. 16, the backing portions 620, 622 have a circumferentially extending tongue 668 that has a radially inwardly facing wall 746 spaced radially inwardly relative to the radially inwardly facing wall 678, and opposite side tongue edge walls 688, 698. The tongue 728 extends circumferentially from the connecting ends 640, 642 of the brake assembly 618 at one end to the free ends 650, 652 at an opposite end.

Figure 18:
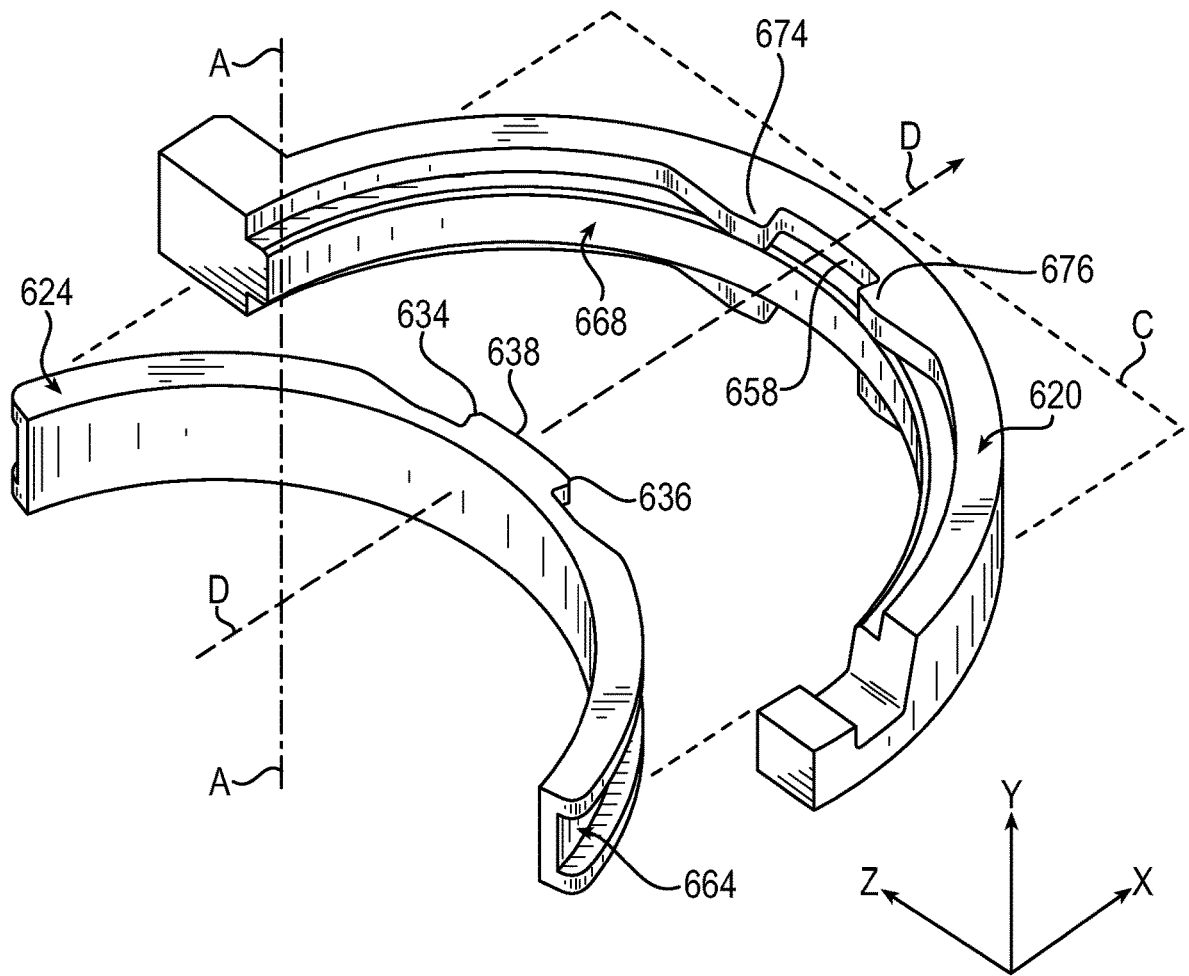
FIG. 18 is a perspective view of the brake assembly of FIG. 14, showing arrangements of components prior to a snap-fitting operation.
Figure 19:
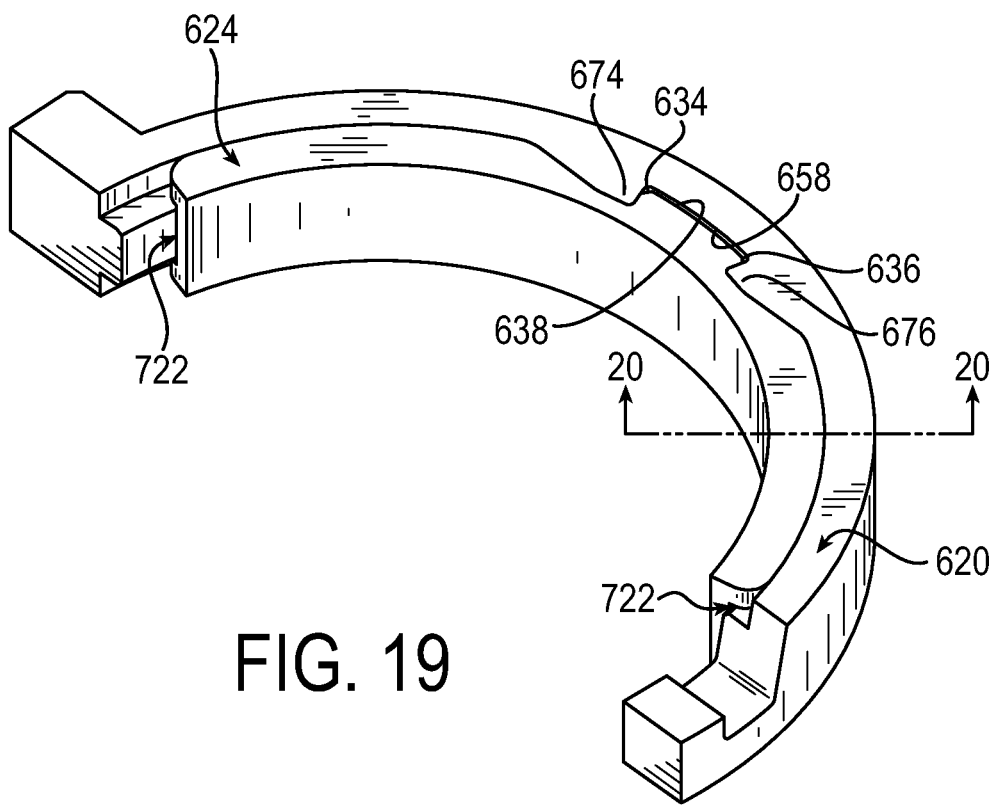
FIG. 19 is a perspective view of the brake assembly of FIG. 14, showing arrangements of components snap-fitted together.
Figure 20:
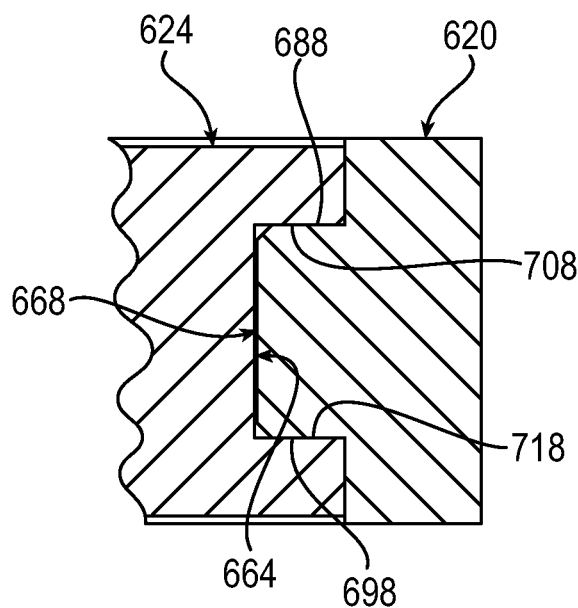
FIG. 20 is a cross-section view of the brake assembly of FIG. 19, as viewed from the plane 20-20 in FIG. 19.

Referring to FIGS. 18-20, it will be appreciated that the circumferential tongue and groove connection 722 resists axial movement of the liners 624, 626 relative to the backing portions 620, 622. As shown in FIG. 20, the tongue edge walls 688, 698 which form part of the backing portion 620 are on axially opposite sides of the groove edge walls 708, 718 in the liner 624. Axial downward movement of the liner 624 is resisted by the groove edge wall 708 abutting the tongue edge wall 688, and axial upward movement of the liner 624 is resisted by the groove edge wall 718 abutting the tongue edge wall 698. In the FIG. 14 brake assembly 618, the axially resisting circumferential tongue and groove connection 722 is located where the tongue 668 axially overlaps the groove 664 around the circumference; that is, on circumferentially opposite sides of where the liners 624, 626 are snap-fitted to the backing portions 620, 622, and at the intermediate portion axially between the protruding parts 634, 636 of the radially protruding dovetails 638. In the latter regard, the protruding parts 634, 636 of the radially protruding dovetails 638 thus are configured to resist radial, circumferential and axial movement of the liner 624, 626 relative to the backing portions 620, 622. In the FIG. 14 embodiment, the circumferential tongue and groove connection 722 corresponds to the location of the pair of flanges 734, 736.

It will be appreciated that the circumferential tongue and groove connection 722 need not be limited to the configuration shown in FIG. 14. For example, the portion axially between the protruding parts 634, 636 of the radially protruding dovetails 638 may constitute one continuous axial structure (i.e. no groove axially between the dovetails 638) and the corresponding intermediate tongue portion may be omitted (i.e. no tongue circumferentially between the bosses 674, 676), so that the circumferential tongue and groove connection 722 is located only at circumferentially opposite sides of where the liners 624, 626 are snap-fitted to the backing portions 620, 622. Alternately, the portion axially between the flanges 734, 735 at the circumferentially opposite sides of where the liners 624, 626 are snap-fitted to the backing portions 620, 622 may constitute one continuous axial structure (i.e. a groove axially between the dovetails 638 but otherwise not axially between the flanges 734, 736) and the corresponding tongue portion at circumferentially opposite sides of where the liners 624, 626 are snap-fitted to the backing portions 620, 622 may be omitted (i.e. a tongue only circumferentially between the bosses 674, 676), so that the circumferential tongue and groove connection 722 is located only at the intermediate portion axially between the protruding parts 634, 636 of the radially protruding dovetails 638. In other embodiments, the groove may be provided in the backing portions 620, 622 and the tongue may be provided on the liners 624, 626.

As was described above with respect to the FIG. 9 embodiment, the first and second arc shape clamp pieces 30, 32 can "float" relative to each other axially, circumferentially, and radially, which floating capability enables the multi-piece split collar to be self-centering and self-aligning relative to the central shaft 14. For clamp pieces that incorporate the backing portions 620, 622 and liners 624, 626 of the FIG. 14 brake assembly 618, the circumferential tongue and groove connection 722 assists in maintaining the integrity of the clamp pieces, so that the liners 624, 626 and backing portions 624, 626 self-center together and self-align together in providing the afore described built-in concentricity clearance between the hub 28 and the brake assembly 618.

Referring still to FIGS. 18-20, an example of snap-fitting a liner 624 to a backing portion 620 (liner 626 and backing portion 622 are omitted in FIGS. 18-20 for purposes of clarity and brevity) will now be described. The liner 624 initially is positioned radially inward of a backing portion 620 with the respective components being in nested relationship and substantially in the same transverse or axial cross sectional plane C. In the illustrative embodiment, the liner 624 is nested relative to the backing portion 620 by the concave portions of the arc shapes of the respective liner 624 and backing portion 620 facing the same direction and the concave portions of the arc shapes of the respective liner 624 and backing portion 620 likewise facing the same direction. The liner 624 and backing portion 620 are then urged together radially until the protruding parts 634, 636 of the radially protruding dovetails 638 of the liner 624 abut or "sit atop" the edges of the bosses 674, 676 on opposite sides of the radially protruding receptacles 658. The dovetails 638 are then fitted into the receptacles 658, so that the protruding parts 634, 636 seat within the undercuts 654, 656 and thereby lock the liner 624 to the backing portion 622. As noted above, any suitable fitting operation may be employed, for example, deflecting both protruding parts 634, 636 before catching in the respective undercuts 654, 656, or inserting one of the protruding parts 634 partially into the respective undercut 654 and deflecting the other of the protruding parts 636 before catching in the respective undercut 656.

As shown in FIG. 20, the tongue 668 and groove 664 of the circumferential tongue and groove connection 722 are configured to slide relative to one another as the liners 624, 626 are snap-fitted to the backing portions 620, 622. In the illustrative embodiment, the tongue 668 is slightly less in width and depth than the groove 664 to facilitate the relative sliding movement. Further, as shown in FIGS. 15 and 20, where the liners 624, 626 are symmetrical about a radial plane B passing through the liner 624, 626 (FIG. 15), so long as a liner 624 is positioned radially inward of a backing portion 620 with the respective components being in nested relationship and substantially in the same transverse or axial cross sectional plane C, the liner 624 can be positioned either as shown in FIG. 18, or at 180 degrees about the axis D-D in FIG. 18. Still further, where the liners 624, 626 have a one part geometry and the backing portions 620, 622 have a one part geometry, the liner 624 can be snap-fitted to either the backing portion 620 or the backing portion 622, and again either as shown in FIG. 18 or 180 degrees about the axis D-D in FIG. 18. As such, assembling the liners 624, 626 to the backing portions 620, 622 is simplified.

FIG. 21 shows a brake assembly 818 according to another embodiment. The brake assembly 818 is similar to the FIG. 14 brake assembly 618 except that the circumferential tongue and groove connection is omitted in the brake assembly 818 and the radially protruding dovetail 838 extends axially from the axial face 904 to the opposite facing axial face 914, and the radially protruding receptacle 858 extends axially from the axial face 884 to the opposite facing axial face 894. Thus, in the FIG. 21 brake assembly 818, there is a single radially protruding dovetail 838 and a single radially protruding receptacle 858. The liners 824, 826 can be snap-fitted to the backing portions 820, 822 in the same manner as described above with respect to the liners 624, 626 and backing portions 620, 622 of the FIG. 14 brake assembly 618. Alternatively, the liners 824, 826 can be connected to the backing portions 820, 822 by axially sliding the radially protruding dovetails 838 into the respective radially protruding receptacles 858.

Figure 22:
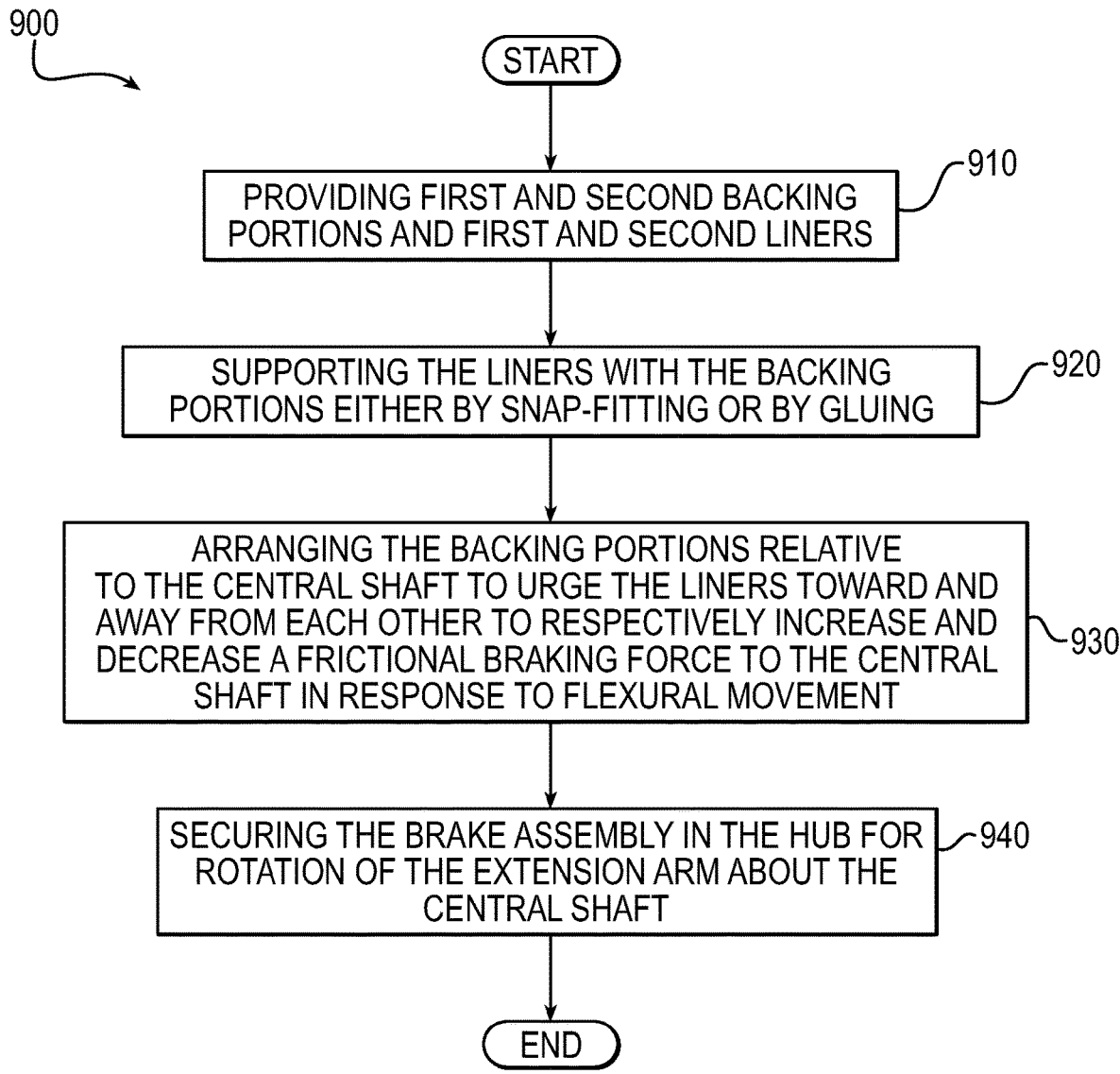
FIG. 22 shows a flowchart of a method of installing a brake assembly in a medical device support system in accordance with an embodiment of the invention.

Referring now to FIG. 22, there is shown a flowchart 900 of a method of installing a brake assembly in a medical device support system, such as the brake assembly 618 in the medical device support system 10 of FIG. 1. At step 910, first and second backing portions 620, 622 and first and second liners 624, 626 of the brake assembly 618 are provided. At step 920, the first and second liners 624, 626 are supported with the respective first and second backing portions 620, 622. This can be done by snap-fitting the first and second liners 624, 626 to the respective first and second backing portions 620, 622, by gluing the first and second liners 624, 626 to the respective first and second backing portions 620, 622, or by snap-fitting the first liner 624 to the first backing portion 620 and gluing the second liner 626 to the second backing portion 622, among others. At step 930, the first and second backing portions 620, 622 are arranged relative to the central shaft 14 to urge the first and second liners 624, 626 toward and away from each other to respectively increase and decrease a frictional braking force to the central shaft 14 in response to flexural movement of the first and second backing portions 620, 622. At step 940, the brake assembly 618 is secured in the hub 128 of the extension arm 16 for rotation with the extension arm 16 about the central shaft 14.

The supporting step 910 can include positioning the first liner 624 radially inward of the first backing portion 620 such that the first liner 624 and first backing portion 620 are in nested relationship and substantially in the same transverse plane. Also, where the first liner 624 includes a dovetail 638 having one or more protruding parts 634, 636 and the first backing portion 620 includes a receptacle 658 having one or more undercuts 654, 656, the supporting step 910 can include fitting the dovetail 638 into the receptacle 658 so that the one or more protruding parts 634, 636 seat within the one or more undercuts 654, 656. Also, where the first liner 624 and first backing portion 620 include a circumferential tongue and groove connection 722, the supporting step 910 can include sliding the tongue 668 and groove 664 relative to one another as the first liner 624 is snap-fitted to the first backing portion 620.

Figure 24:
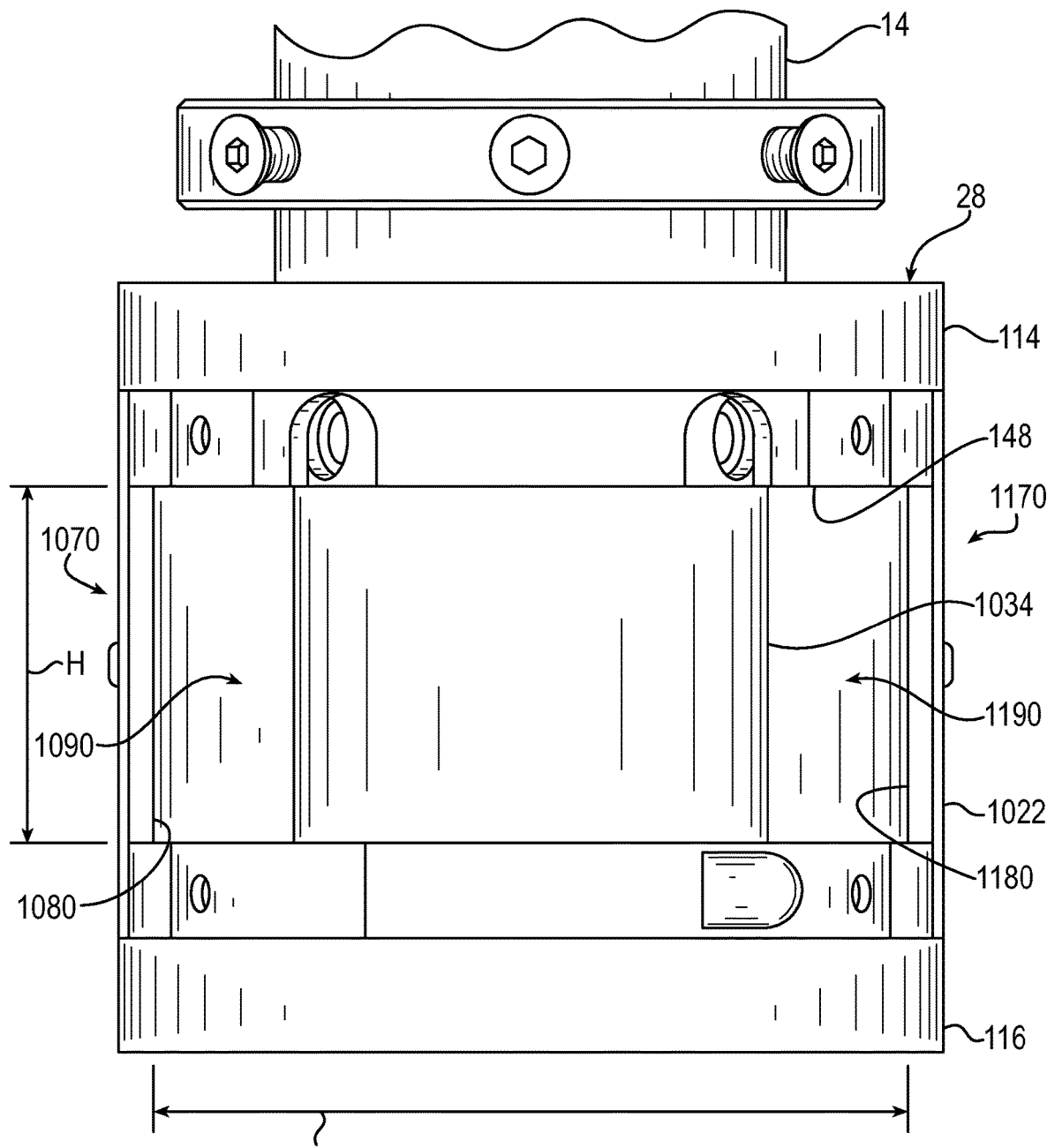
FIG. 24 is a side elevational view of the medical device support system of FIG. 1, as viewed from the plane 24-24 in FIG. 2, showing a hub access opening in greater detail.

FIGS. 23-33 show in greater detail the hub 28 of the extension arm 16 and a hub access opening 148 according to an embodiment of the invention. The hub access opening 148 is configured to allow insertion and removal of the brake assembly 18 therethrough, and more particularly one or more of the first and second arc shape clamp pieces 30, 32, both clamp pieces 30, 32 in the illustrative embodiment, therethrough. FIG. 23 shows the first and second arc shape clamp pieces 30, 32 in an assembled state for brake assembly function, and in this state the actuator 70, FIG. 2, is configured to flex the first and second clamp pieces 30, 32 toward and away from each other to respectively increase and decrease the frictional braking force to the central shaft 14. A radial gap 1010 may be provided between an inner perimeter 1016 of the hub 28 and an outer periphery 1018 of the first and second arc shape clamp pieces 30, 32 to allow the first and second arc shape clamp pieces 30, 32 to flex radially between the inner periphery 1016 of the hub 28 and the central shaft 14. As shown in FIGS. 23 and 24, the hub access opening 148 protrudes radially through an outer wall 1022 of the hub 28 and, as will be described in greater detail below, is configured to allow passage of the first and second arc shape clamp pieces 30, 32 radially therethrough such that the clamp pieces 30, 32 can be arranged relative to the central shaft 14 to perform braking functions. The hub access opening 148 is disposed axially between the upper and lower bearing mounts 114, 116, FIG. 3, that house the respective first and second pivot bearings mounted to the central shaft 14. In the illustrative embodiment, the hub access opening 148 has an arc shape in axial cross section and has a radius substantially the same as the radius of the outer wall 1022 of the hub 28. An arc shape panel 1030, shown in FIG. 23, may be attached to the outer wall 1022 by suitable fasteners 1032 to cover the hub access opening 148. As will be appreciated, the hub access opening 148 simplifies and adds efficiency to the factory assembly and field service of the medical device support system 10, for example, by allowing easy insertion and removal of the brake assembly 18 components.

The hub access opening 148 and the radial extent 138 of the extension arm 16 are diametrically opposed from one another so that the hub access opening 148 is "out of the way" from the extension arm 16, providing more free space or working space in front of the hub access opening 148. In other embodiments, the hub access opening 148 may be positioned angularly offset from the radial extent 138 by other than diametrically opposed, for example, by 90 degrees. The hub access opening 148 allows access to the interior of the hub 28 and the brake assembly 18 and other components therein without compromising the functionality or structural integrity of the hub 28 or the extension arm 16 of which it is a part.

Figure 25:
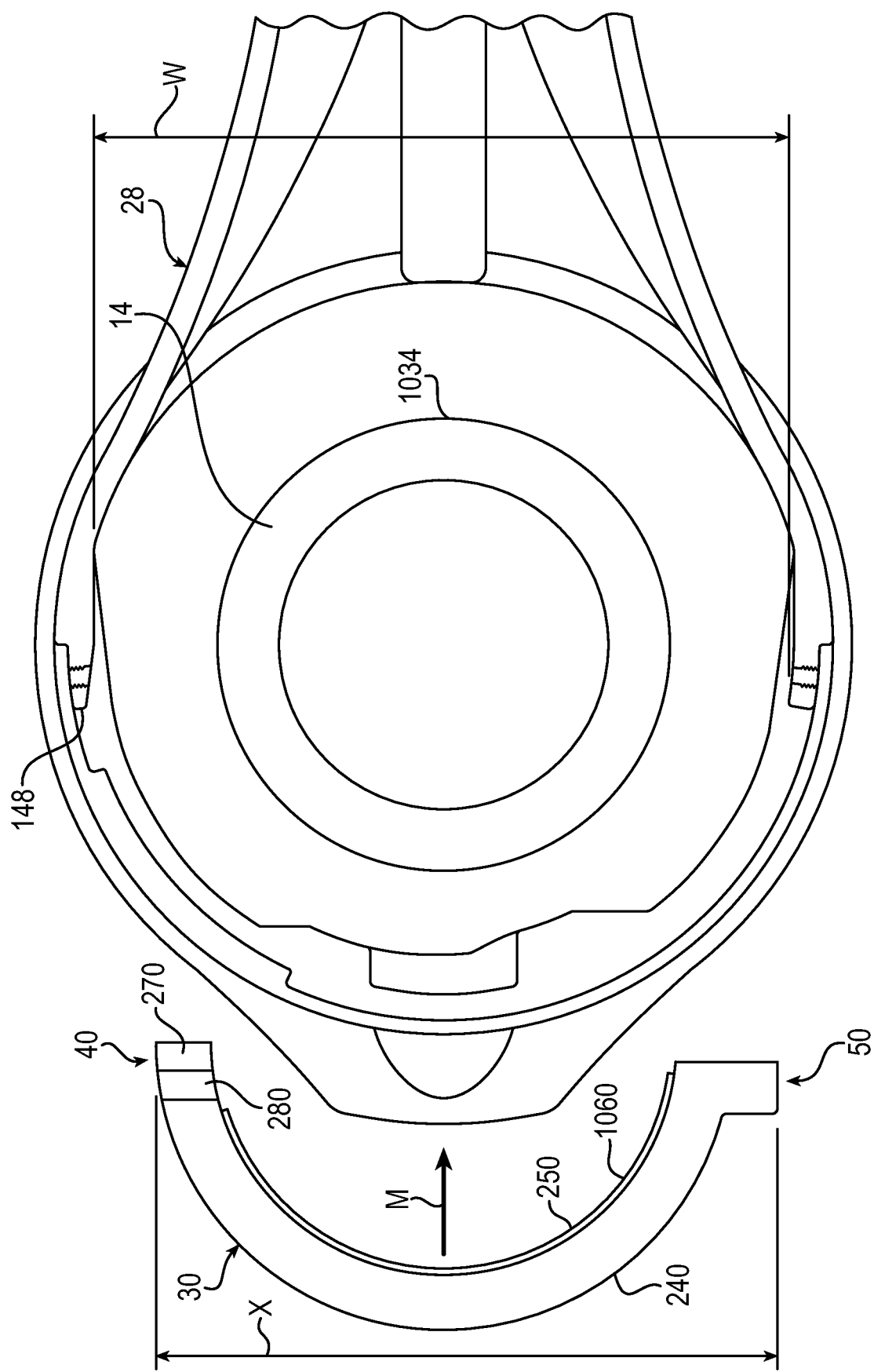
FIG. 25 is a view similar to FIG. 23, showing an arc shape clamp piece positioned radially outward from a hub access opening.
Figure 26:
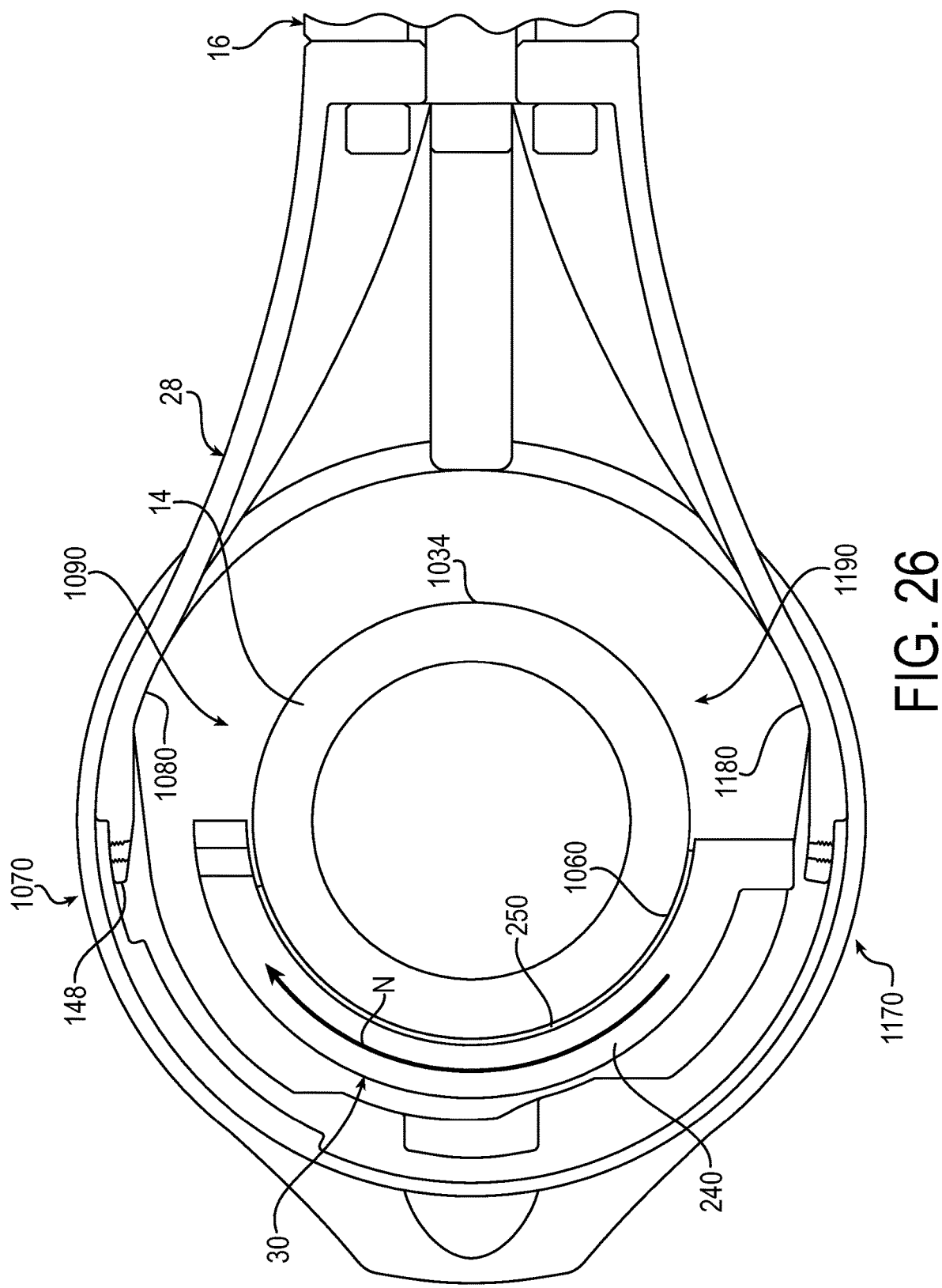
FIG. 26 is a view similar to FIG. 23, showing an arc shape clamp piece having been inserted radially through a hub access opening from the position shown in FIG. 25, and abutting a central shaft of the medical device support system.

As shown in FIGS. 25 and 26, the hub access opening 148 allows insertion of the first arc shape clamp piece 30 radially through the hub access opening 148, as indicated by arrow M, until the arc shape liner 250 of the first arc shape clamp piece 30 abuts or nearly abuts an outer periphery 1034 of the central shaft 14. This may be enabled for example by the hub access opening 148 having an axial height H, FIG. 24, that is greater than the axial height J, FIGS. 28 and 32, of the first arc shape clamp piece 30, and a width W, FIGS. 23 and 25, in axial cross section that is greater than a width X, FIG. 25, of the first arc shape clamp piece 30 in axial cross section from the free end 50 to the connecting end 40 of the first arc shape clamp piece 30. As shown in FIG. 25, and with reference to FIGS. 9 and 10, the first arc shape clamp piece 30 is inserted into the hub access opening 148 such that its axially extending tab 270 protrudes axially upward and its axially extending notch 280 opens axially upward.

The first arc shape clamp piece 30 is inserted into the hub access opening 148 and positioned relative to the central shaft 14 to allow the first arc shape clamp piece 30 subsequently to be rotated about the central shaft 14 and axially moved to the brake assembly position. In FIG. 26, a radially inner surface 1060 of the arc shape liner 250 is shown in abutting relation with the outer periphery 1034 of the central shaft 14. In the illustrative embodiment, the central shaft 14 at the abutting location has a circular shape; as such, the outer periphery 1034 constitutes an outer diameter of the central shaft 14. By matching the radius of the central shaft 14 substantially to the radius of the inner surface 1060 of the arc shape liner 250, at least at the axial location radially adjacent to the hub access opening 148, the first arc shape clamp piece 30 can be rotated about the central shaft 14 fairly smoothly. It will be appreciated that the central shaft 14 at the axial location radially adjacent to the hub access opening 148 may have an outer periphery 1034 that does not necessarily match that of the radially inner surface 1060 of the arc shape liner 250. For example, the central shaft 14 may have a relatively smaller radius in the axial location radially adjacent to the hub access opening 148 that gradually merges into a relatively larger radius suited for the brake assembly function either therebelow or thereabove. In this regard, the outer periphery 1034 of the central shaft 14 at the axial location radially adjacent to the hub access opening 148 may be different than the outer periphery 230 of the central shaft 14 at the brake assembly location. It will further be appreciated that the first arc shape clamp piece 30 can be slightly radially spaced from, or nearly abutting, the outer periphery 1034 of the central shaft 14, and/or in partially abutting relation to the outer periphery 1034 of the central shaft 14, so long as the first arc shape clamp piece 30 can be rotated about the central shaft 14.

Figure 27:
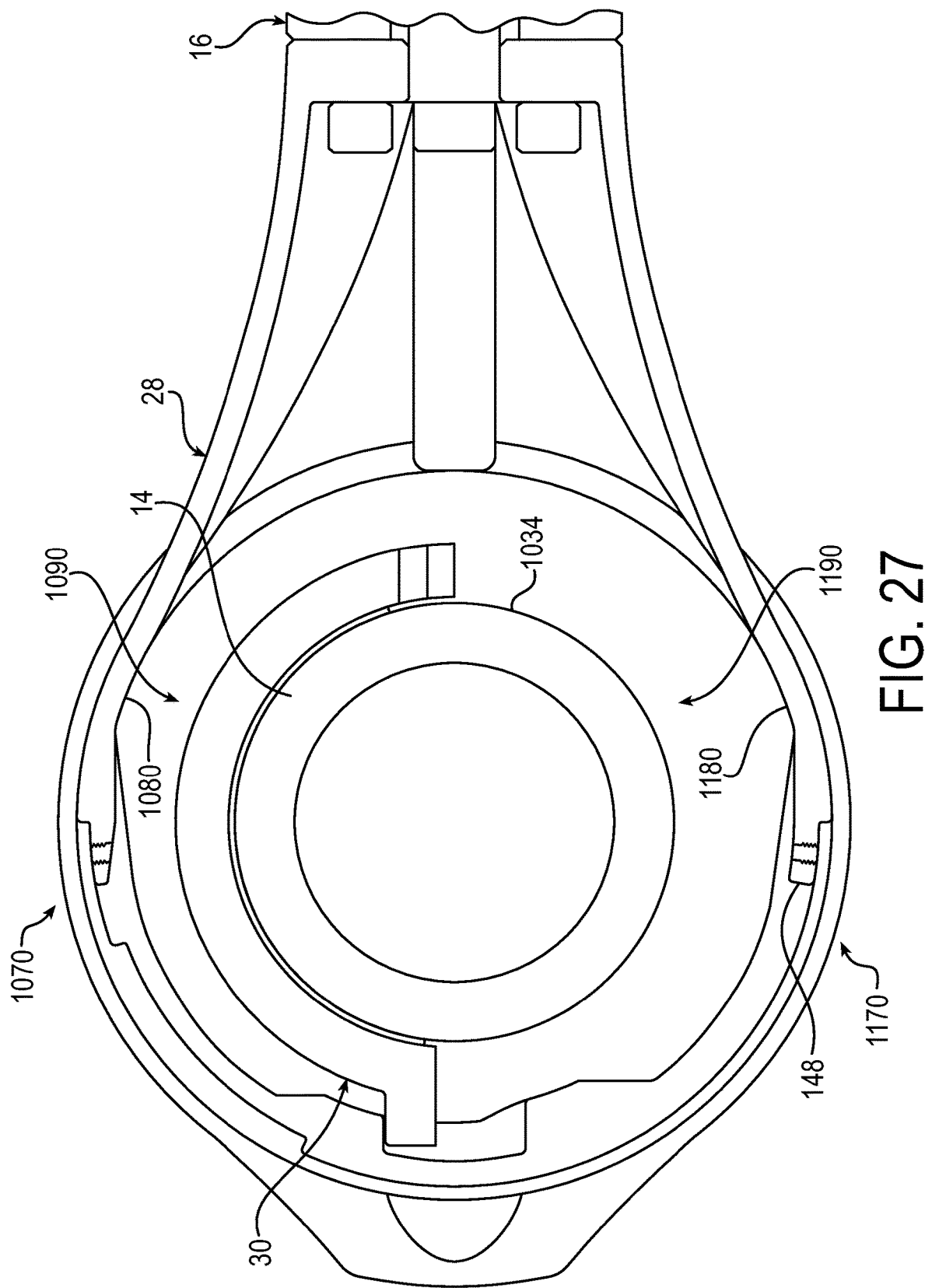
FIG. 27 is a view similar to FIG. 23, showing an arc shape clamp piece having been rotated clockwise from the position shown in FIG. 26.

The first arc shape clamp piece 30, once positioned relative to the central shaft 14, for example in abutting contact with the central shaft 14 as shown in FIG. 26, can be rotated or "clocked," as indicated by arrow N in FIG. 26, to an appropriate angular position as shown in FIG. 27 where the first arc shape clamp piece 30 subsequently can be axially moved to the brake assembly position. In FIGS. 26-27, the first arc shape clamp piece 30 is rotated clockwise 90 degrees. As shown in FIGS. 24, 26 and 27, on a circumferentially adjacent side 1070 of the hub access opening 148, an inner periphery 1080 of the hub 28 and the outer periphery 1034 of the central shaft 14 define a space 1090 to allow the first arc shape clamp piece 30 to be rotated at least partially about the central shaft 14.

Figure 28:
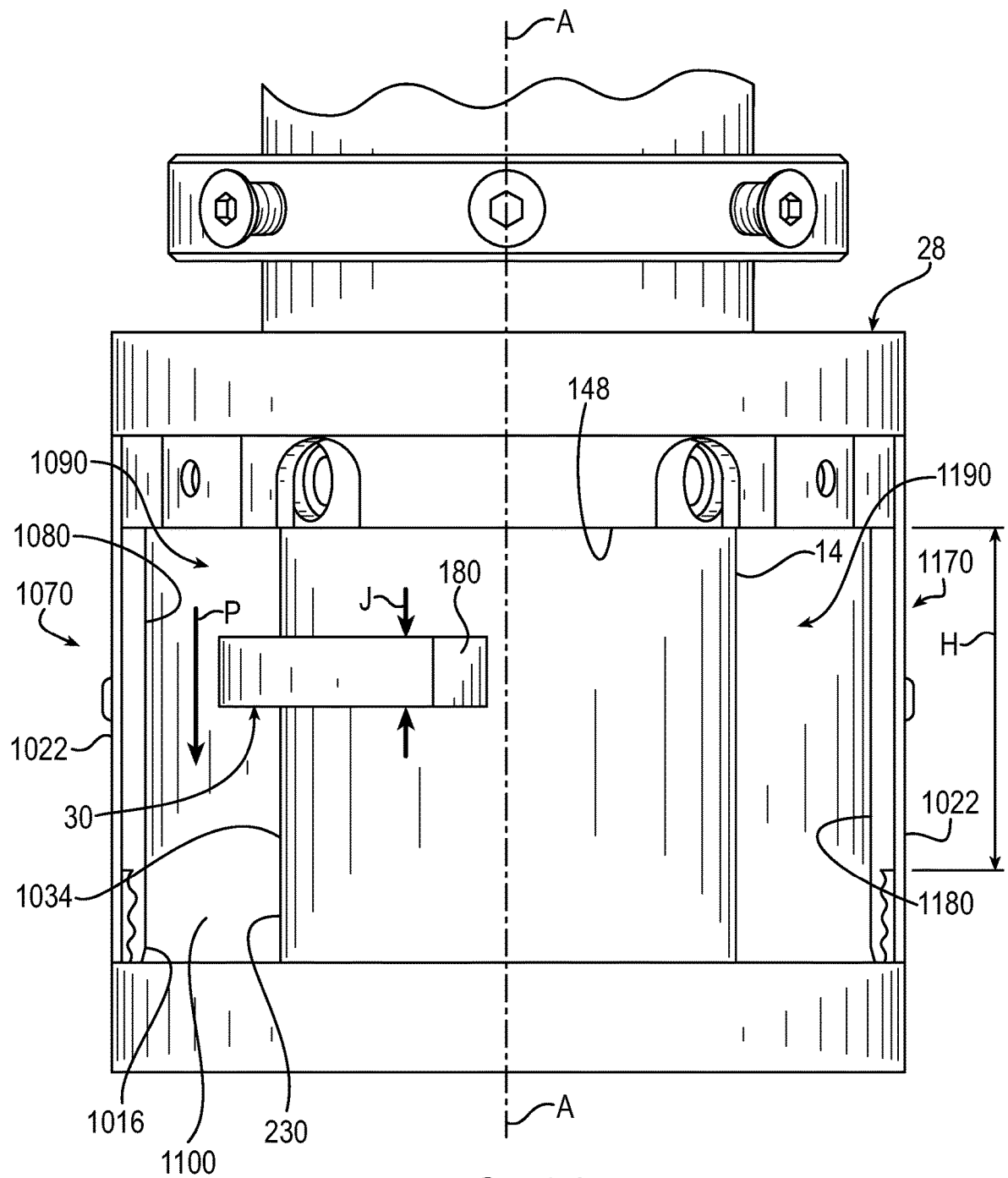
FIG. 28 is a view similar to FIG. 24, showing an arc shape clamp piece positioned axially above an edge of a hub access opening.
Figure 32:
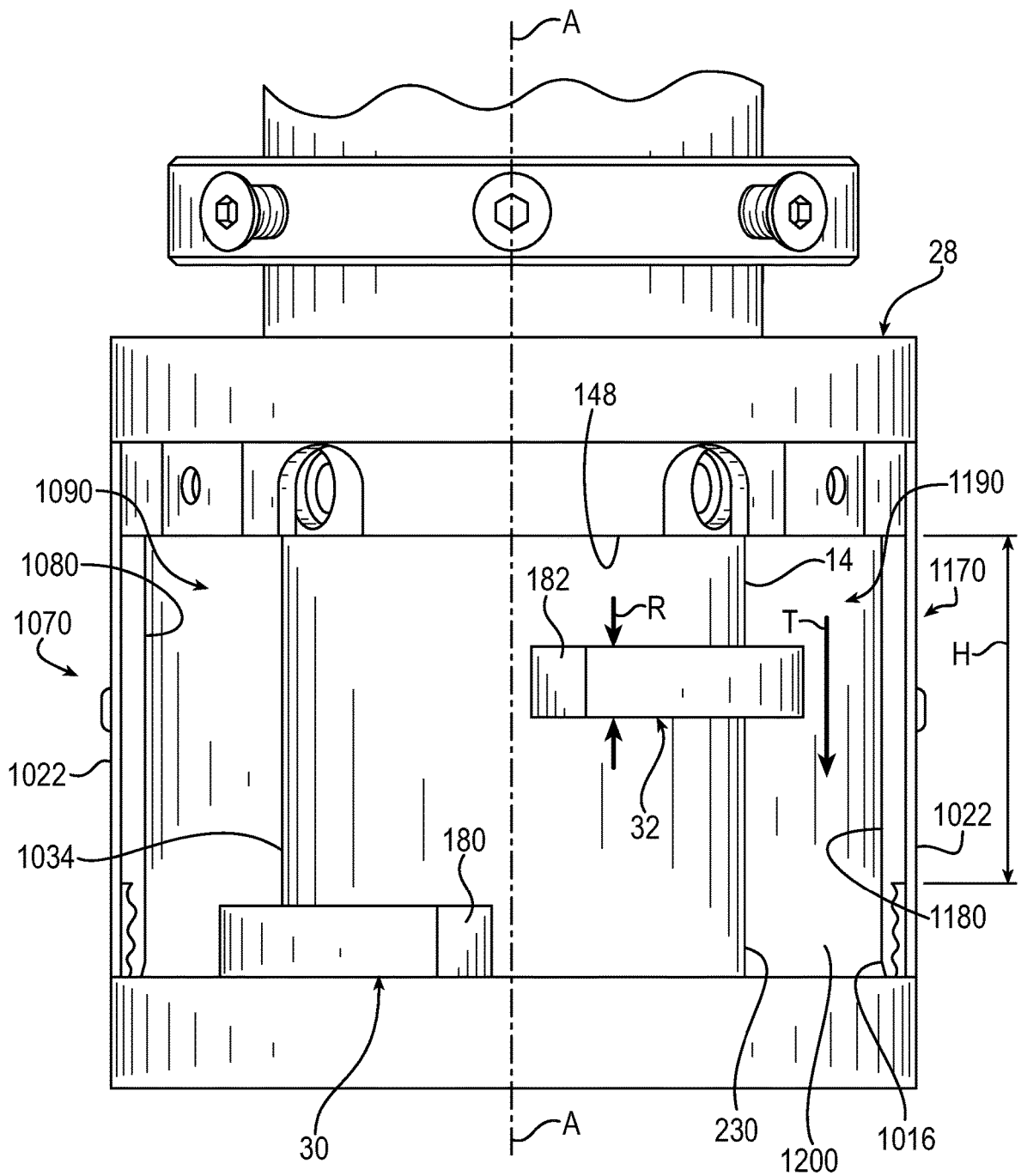
FIG. 32 is a view similar to FIG. 24, showing one arc shape clamp piece positioned axially below a hub access opening, and another arc shape clamp piece positioned axially above an edge of the hub access opening.

FIGS. 27 and 28 show the first arc shape clamp piece 30 in the appropriate angular position to be axially moved to the brake assembly position. Referring to FIGS. 23 and 28, axially adjacent to the hub access opening 148, in the illustrative embodiment axially below the hub access opening 148, the inner periphery 1016 of the hub 28 and the outer periphery 230 of the central shaft 14 define a space 1100 to allow the first arc shape clamp piece 30 to be moved axially to the position axially adjacent to the hub access opening 148. FIGS. 28 and 32 show the first arc shape clamp piece 30 moved from the hub access opening 148 area to the brake assembly position therebelow, as indicated by arrow P in FIG. 28. Referring to FIG. 23, the inner periphery 1016 of the hub 28 defines the radially protruding notch 186, which is axially adjacent, axially below in FIGS. 24 and 28, the hub access opening 148 and is configured to receive the radially protruding tab 180 of the first arc shape clamp piece 30.

Figure 29:
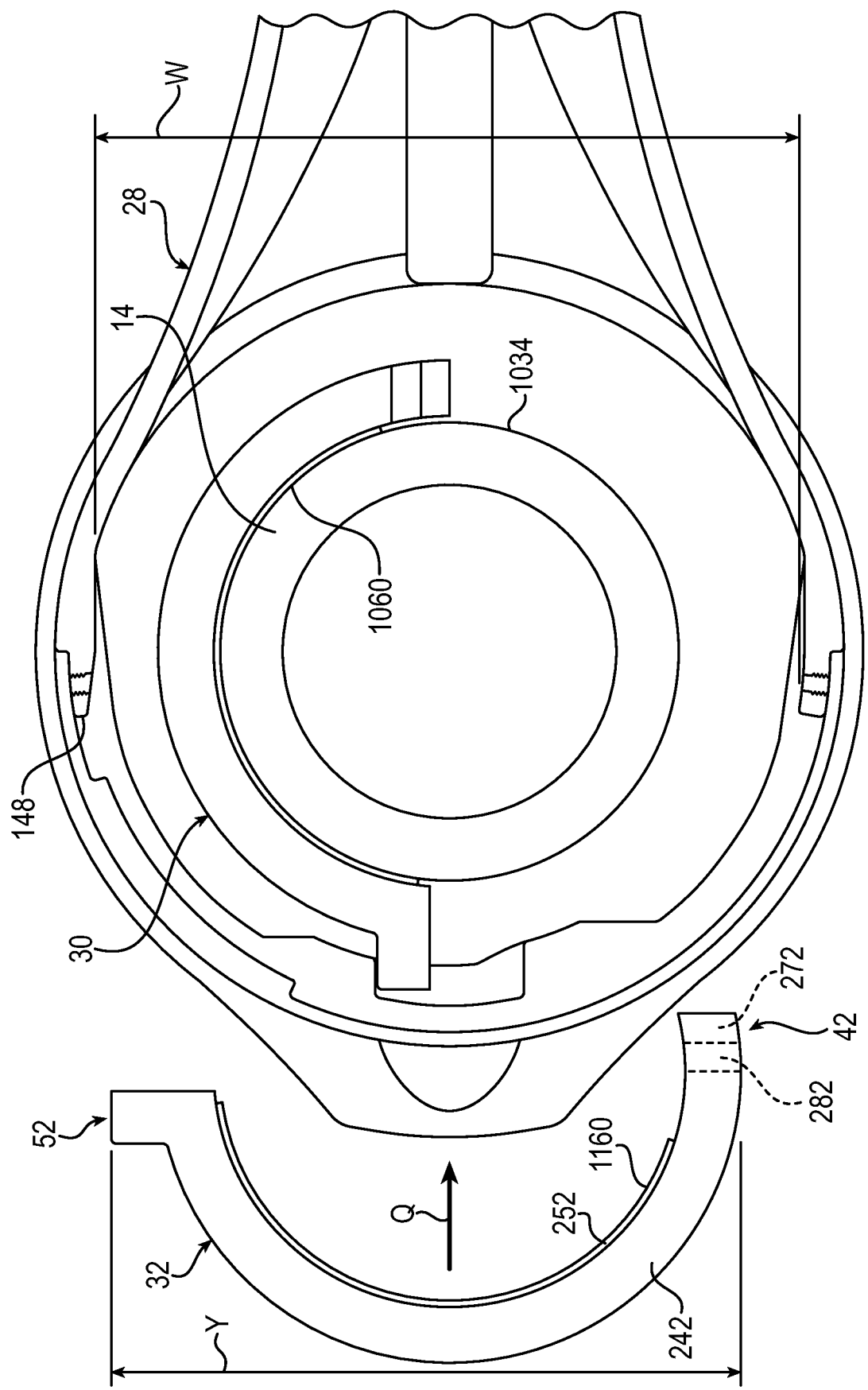
FIG. 29 is a view similar to FIG. 23, showing an arc shape clamp piece positioned radially outward from a hub access opening.
Figure 30:
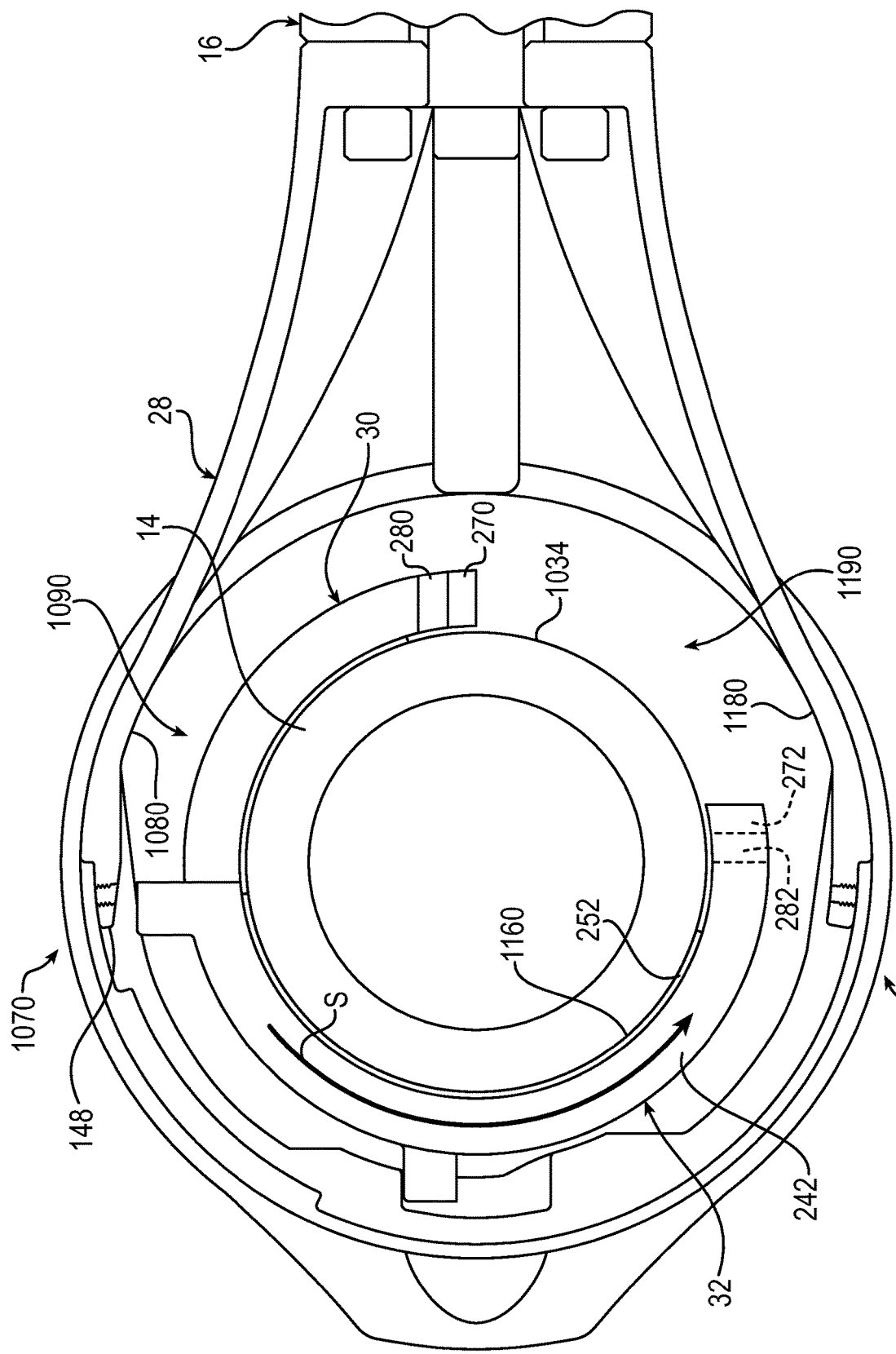
FIG. 30 is a view similar to FIG. 23, showing an arc shape clamp piece having been inserted radially through a hub access opening from the position shown in FIG. 29, and abutting a central shaft of the medical device support system.

Referring now to FIGS. 29 and 30, the hub access opening 148 may also allow insertion of the second arc shape clamp piece 32 radially through the hub access opening 148, as indicated by arrow Q, until the arc shape liner 252 of the second arc shape clamp piece 32 abuts or nearly abuts the outer periphery 1034 of the central shaft 14. This may be enabled in a similar manner as the first arc shape clamp piece 30 particularly where the geometry of the first and second arc shape clamp pieces 30, 32 may be identical. Thus, for example, the hub access opening 148 may have an axial height H, FIG. 24, that is greater than the axial height R, FIG. 32, of the second arc shape clamp piece 32, and a width W, FIGS. 23 and 29, in axial cross section that is greater than a width Y, FIG. 29, of the second arc shape clamp piece 32 in axial cross section from the free end 52 to the connecting end 42 of the second arc shape clamp piece 32. As shown in FIG. 29, and with reference to FIGS. 9 and 10, the second arc shape clamp piece 32 is inserted into the hub access opening 148 such that its axially extending tab 272 protrudes axially downward and its axially extending notch 282 opens axially downward.

The second arc shape clamp piece 32 is inserted into the hub access opening 148 and positioned relative to the central shaft 14 to allow the second arc shape clamp piece 32 subsequently to be rotated about the central shaft 14 and axially moved to the brake assembly position. In FIG. 30, a radially inner surface 1160 of the arc shape liner 252 is shown in abutting relation with the outer periphery 1034 of the central shaft 14. As was described above with respect to the first arc shape clamp piece 30, and since the radial insertion of the second arc shape clamp piece 32 occurs at substantially the same axial location as that of the first arc shape clamp piece 30, the central shaft 14 at the abutting location has a circular shape and thus the outer periphery 1034 constitutes an outer diameter of the central shaft 14. By matching the radius of the central shaft 14 substantially to the radius of the inner surface 1160 of the arc shape liner 252, at least at the axial location radially adjacent to the hub access opening 148, the second arc shape clamp piece 32 can be rotated about the central shaft 14 fairly smoothly. It will be appreciated that the central shaft 14 at the axial location radially adjacent to the hub access opening 148 may have an outer periphery 1034 that does not necessarily match that of the radially inner surface 1160 of the arc shape liner 252. For example, the central shaft 14 may have a relatively smaller radius in the axial location radially adjacent to the hub access opening 148 that gradually merges into a relatively larger radius suited for the brake assembly function either therebelow or thereabove. In this regard, the outer periphery 1034 of the central shaft 14 at the axial location radially adjacent to the hub access opening 148 may be different than the outer periphery 230 of the central shaft 14 at the brake assembly location. It will further be appreciated that the second arc shape clamp piece 32 can be slightly radially spaced from, or nearly abutting, the outer periphery 1034 of the central shaft 14, and/or in partially abutting relation to the outer periphery 1034 of the central shaft 14, so long as the second arc shape clamp piece 32 can be rotated about the central shaft 14.

Figure 31:
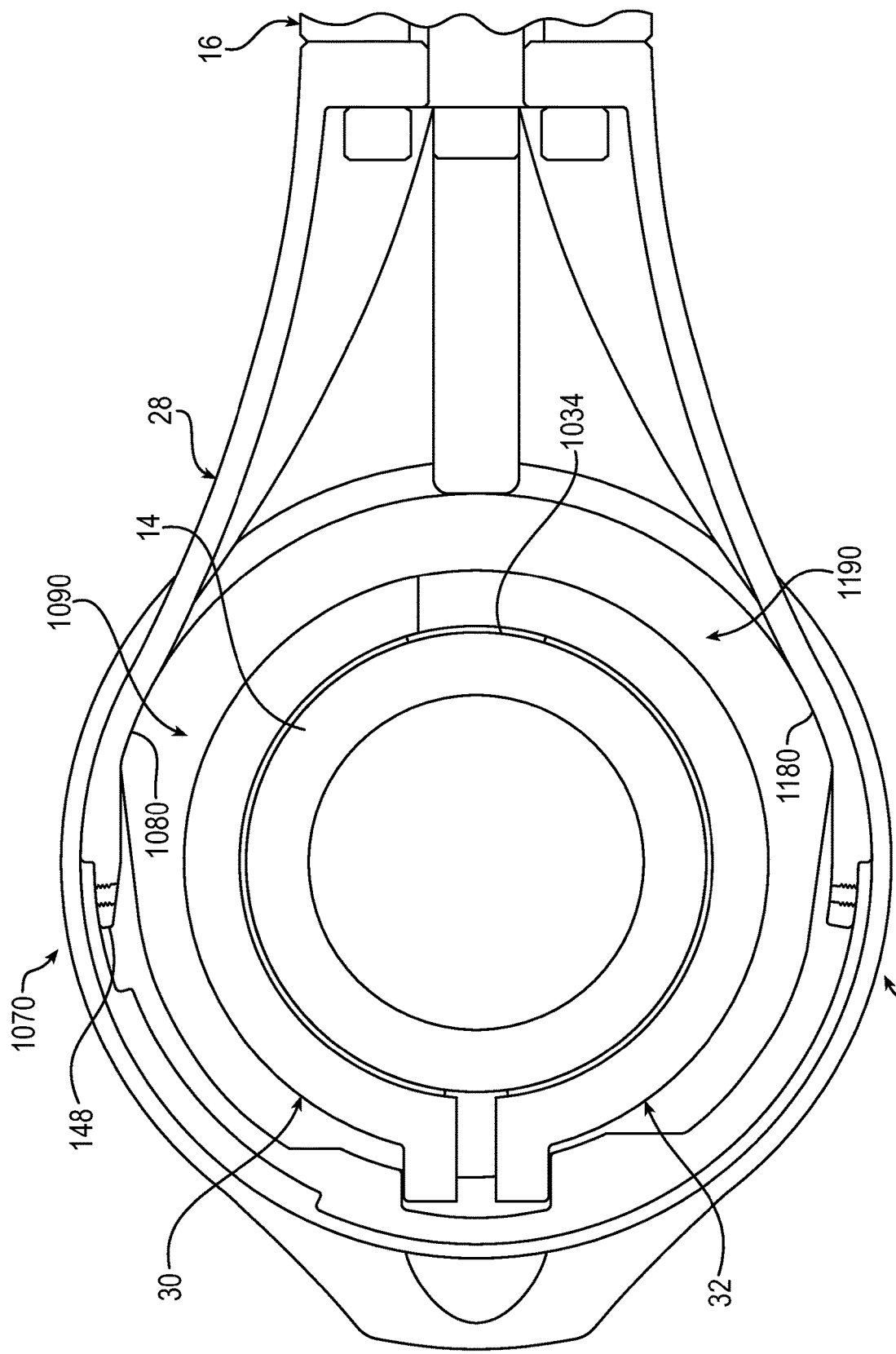
FIG. 31 is a view similar to FIG. 23, showing an arc shape clamp piece having been rotated counterclockwise from the position shown in FIG. 30.

The second arc shape clamp piece 32, once positioned relative to the central shaft 14, for example in abutting contact with the central shaft 14 as shown in FIG. 30, can be rotated or "clocked," as indicated by arrow S in FIG. 30, to an appropriate angular position as shown in FIG. 31 where the second arc shape clamp piece 32 subsequently can be axially moved to the brake assembly position. In FIGS. 30-31, the second arc shape clamp piece 32 is rotated counterclockwise 90 degrees. As shown in FIGS. 24, 30 and 31, on a circumferentially adjacent side 1170 of the hub access opening 148, an inner periphery 1180 of the hub 28 and the outer periphery 1034 of the central shaft 14 define a space 1190 to allow the second arc shape clamp piece 32 to be rotated at least partially about the central shaft 14.

As shown in FIGS. 26 and 30, the first arc shape clamp piece 30 is rotated clockwise, arrow N, about the central shaft 14, whereas the second arc shape clamp piece 32 is rotated in an opposite direction from that of the first arc shape clamp piece 30, or counterclockwise, arrow S. It will be appreciated that the rotation may be other than that shown in FIGS. 26 and 30. For example, in FIG. 26, the first arc shape clamp piece 30 can instead be rotated counterclockwise, for example 270 degrees, and the second arc shape clamp piece 32 can instead be rotated clockwise, for example 270 degrees. Further, it will be appreciated that where the hub access opening 148 is positioned angularly offset from the radial extent 138 of the extension arm 16 by other than diametrically opposed, the degree of rotation of the first and second claim pieces 30, 32 may be other than 90 degrees (or other than 270 degrees).

Figure 33:
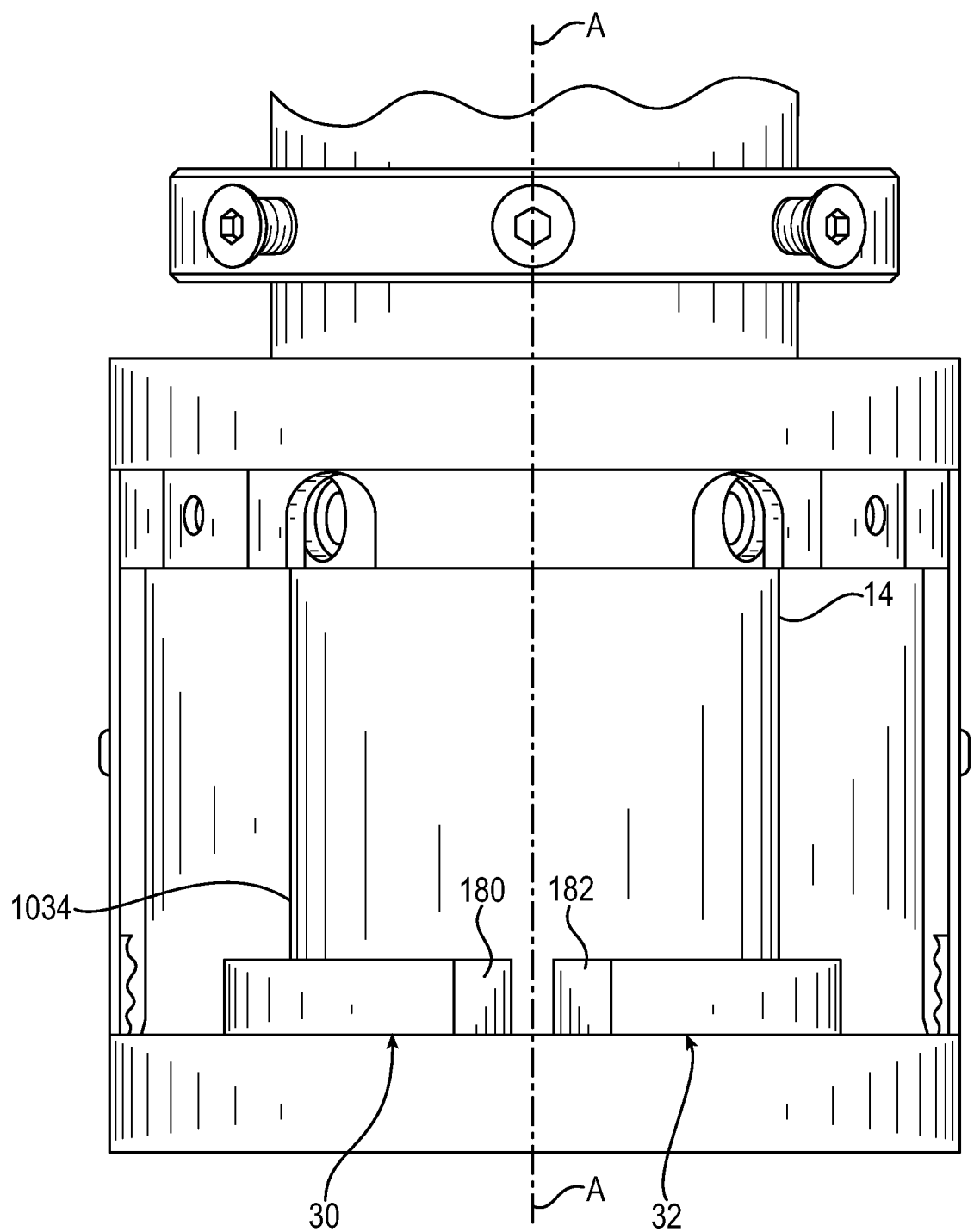
FIG. 33 is a view similar to FIG. 24, showing one arc shape clamp piece positioned axially below a hub access opening, and another arc shape clamp piece positioned axially below the hub access opening.

FIGS. 31 and 32 show the second arc shape clamp piece 32 in the appropriate angular position to be axially moved to the brake assembly position. Referring to FIGS. 23 and 32, axially adjacent to the hub access opening 148, in the illustrative embodiment axially below the hub access opening 148, the inner periphery 1016 of the hub 28 and the outer periphery 230 of the central shaft 14 define a space 1200 to allow the second arc shape clamp piece 32 to be moved axially to the position axially adjacent to the hub access opening 148. FIGS. 32 and 33 show the second arc shape clamp piece 32 moved from the hub access opening 148 area to the brake assembly position therebelow, as indicated by arrow T in FIG. 32. Referring to FIG. 23, the inner periphery 1016 of the hub 28 defines the radially protruding notch 186, which is axially adjacent, axially below in FIGS. 24 and 32, the hub access opening 148 and is configured to receive the radially protruding tab 182 of the second arc shape clamp piece 32.

Referring now to FIGS. 9, 10 and 23, since the first arc shape clamp piece 30 is inserted into the hub access opening 148 such that its axially extending tab 270 protrudes axially upward and its axially extending notch 280 opens axially upward, and the second arc shape clamp piece 32 is inserted into the hub access opening 148 such that its axially extending tab 272 protrudes axially downward and its axially extending notch 282 opens axially downward, when the second arc shape clamp piece 32 is lowered to the brake assembly position, the tab 272 is slidably received into the notch 280 and the tab 270 is slidably received into the notch 282, thus forming the coupling joint 46 that functions as the joint relative to which the arc shape clamp pieces 30, 32 flex.

As was noted above with respect to FIGS. 2, 5, 9 and 10, the initial assembly of the interlocking split that forms the coupling joint 46, and the insertion of the tabs 180, 182 in the hub notch 186, may take on a variety of forms. In one form, in the initial assembly of the interlocking split and insertion of the tabs 180, 182 in the hub notch 186, the axially extending tabs 270, 272 may be circumferentially separate from one another such that the arc shape clamp pieces 30, 32 are in an unflexed or relaxed state. In another form, in the initial assembly of the interlocking split and insertion of the tabs 180, 182 in the hub notch 186, the axially extending tabs 270, 272 may be in circumferentially abutting relation at the opposite facing walls 290, 292 such that the arc shape clamp pieces 30, 32 are in a slightly flexed state. In any event, the actuator 70 may then be used to urge the first and second arc shape clamp pieces 30, 32 toward one another thereby to impart the desired frictional braking force to the central shaft 14.

In FIG. 33, the brake assembly 18 is secured in the hub 28 in a position axially below the hub access opening 148. It will be appreciated that the configuration need not be limited as such and other embodiments are contemplated. For example, the brake assembly 18 can be secured in the hub 31 in a position axially above the hub access opening 148, in which case, as described above, a retaining ring may be mounted in a groove in the central shaft 14 immediately below, or a slight clearance below, the first and second arc shape clamp pieces 30, 32 to axially retain or guide the arc shape clamp pieces 30, 32 relative to the central shaft 14. In another example, a brake assembly 18 may be provided axially below the hub access opening 148 and another brake assembly 18 may be provided axially above the hub access opening 148, for example, where a need for multiple brake assemblies can provide more stability or is otherwise desired. In any event, the hub access opening 148 can receive the first and second arc shape clamp pieces 30, 32 radially therethrough.

It will also be appreciated that the first and second arc shape clamp pieces 30, 32 may be inserted into the hub access opening 148 in multiple parts. For example, the arc shape backing piece 240 may be inserted through the hub access opening 148, followed by the liner 250 being inserted through the hub access opening 148. The liner 250 can then be attached to the backing piece 240 to form a first arc shape clamp piece 30, and then the first arc shape clamp piece 30 can be rotated and moved to the brake assembly position. The same can be done with respect to the arc shape backing piece 242 and the liner 252. It will be appreciated that the same also could be done with respect to the above described snap-fit configurations; that is, the liner can be snap-fitted to the backing portion prior or subsequent to the backing portion being inserted through the hub access opening.

Figure 34:
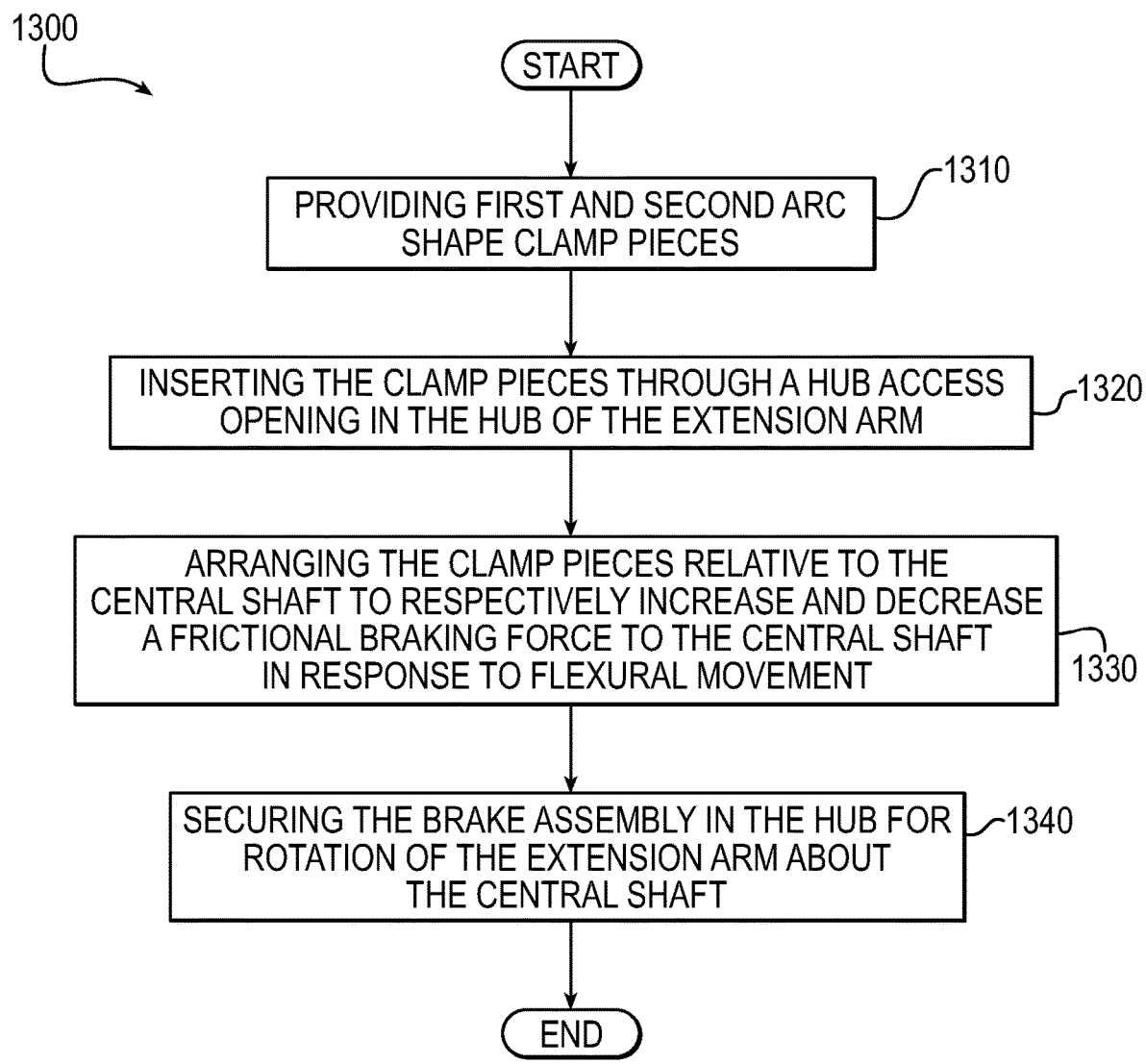
FIG. 34 shows a flowchart of a method of installing a brake assembly in a medical device support system in accordance with an embodiment of the invention.

Referring now to FIG. 34, there is shown a flowchart 1300 of a method of installing a brake assembly in a medical device support system, such as the brake assembly 18 in the medical device support system 10 of FIG. 1. At step 1310, first and second discrete arc shape clamp pieces 30, 32 of the brake assembly 18 are provided. At step 1320, the first and second arc shape clamp pieces 30, 32 are inserted through a hub access opening 148 in the hub 28 of the extension arm 16. At step 1330, the first and second arc shape clamp pieces 30, 32 are arranged relative to the central shaft 14 to respectively increase and decrease a frictional braking force to the central shaft 14 in response to flexural movement of the first and second arc shape clamp pieces 30, 32. At step 1340, the brake assembly 18 is secured in the hub 28 of the extension arm 16 for rotation with the extension arm 16 about the central shaft 14.

The inserting step 1320 can include inserting the first and second arc shape clamp pieces 30, 32 radially through the hub access opening 148 until an inner liner 250 abuts or nearly abuts the central shaft 14. The arranging step 1330 can include rotating the first and second arc shape clamp pieces 30, 32 at least partially about the central shaft 14. The arranging step 1330 can include moving the first and second arc shape clamp pieces 30, 32 to a position axially adjacent to the hub access opening 148. The arranging step 1330 can include inserting first and second radially protruding tabs 180, 182 of the respective first and second arc shape clamp pieces 30, 32 into a radially protruding notch 186 in the hub 28 to a position axially adjacent to the hub access opening 148. The arranging step 1330 may include sliding axially the first and second arc shape clamp pieces 30, 32 relative to one another.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A medical device support system, comprising:
   a central shaft;
   an extension arm having a support for a medical device and a hub at its proximal end mounted to the central shaft for pivotable movement about the central shaft; and,
   a brake assembly secured in the hub for rotation therewith and including first and second discrete arc shape clamp pieces configured to flex toward and away from each other to respectively increase and decrease a frictional braking force to the central shaft;
   wherein the hub includes a hub access opening configured to allow passage therethrough of at least one of the arc shape clamp pieces.

2. The medical device support system of claim 1, wherein the brake assembly includes an actuator configured to flex the first and second clamp pieces toward and away from each other to respectively increase and decrease the frictional braking force to the central shaft.

3. The medical device support system of claim 1, wherein the hub includes axially spaced first and second bearing mounts that house respective first and second pivot bearings mounted to the central shaft, and wherein the hub access opening is disposed axially between the first and second bearing mounts.

4. The medical device support system of claim 1, wherein the hub access opening has an arc shape in axial cross section and has a radius that is substantially the same as a radius of an outer wall of the hub.

5. The medical device support system of claim 1, wherein a radial gap is provided between an inner periphery of the hub and an outer periphery of the first and second arc shape clamp pieces to allow the first and second arc shape clamp pieces to be moved radially between the inner periphery of the hub and the central shaft.

6. The medical device support system of claim 1, wherein the hub access opening protrudes radially through a wall in the hub and is configured to allow passage of the arc shape clamp piece radially therethrough until an arc shape liner of the arc shape clamp piece abuts or nearly abuts the central shaft.

7. The medical device support system of claim 1, wherein, on a circumferentially adjacent side of the hub access opening, an inner periphery of the hub and an outer periphery of the central shaft define a space to allow the at least one arc shape clamp piece to be rotated at least partially about the central shaft.

8. The medical device support system of claim 1, wherein axially adjacent to the hub access opening an inner periphery of the hub and an outer periphery of the central shaft define a space to allow the at least one arc shape clamp piece to be moved axially to a position axially adjacent to the hub access opening.

9. The medical device support system of claim 8, wherein the inner periphery of the hub defines a radially protruding notch that is configured to receive a radially protruding tab of the at least one arc shape clamp piece, wherein the radially protruding notch is axially adjacent to the hub access opening.

10. The medical device support system of claim 1, wherein when the first and second clamp pieces are flexed toward each other to increase the frictional braking force to the central shaft, the first and second clamp pieces have an arc shape contact with the outer periphery of the central shaft.

11. An extension arm for a medical device support system having a central shaft, the extension arm comprising:
   a support for a medical device;
   a hub at a proximal end of the extension arm, the hub being mountable to the central shaft for pivotable movement about the central shaft; and,
   a brake assembly secured in the hub for rotation therewith and including first and second discrete arc shape clamp pieces configured to flex toward and away from each other to respectively increase and decrease a frictional braking force to the central shaft;
   wherein the hub includes a hub access opening configured to allow passage therethrough of at least one of the arc shape clamp pieces.

12. The extension arm of claim 11, wherein the hub access opening and a radial extent of the arm are diametrically opposed from one another.

13. The extension arm of claim 11, wherein the hub access opening protrudes radially through a wall in the hub and is configured to allow passage of the arc shape clamp piece radially therethrough.

14. The extension arm of claim 11, wherein the hub access opening has an axial height that is greater than the axial height of the arc shape clamp piece.

15. The extension arm of claim 11, wherein the hub access opening has a width in axial cross section that is greater than a width of the arc shape clamp piece in axial cross section from a free end to a connecting end of the arc shape clamp piece.

16. The extension arm of claim 11, wherein the brake assembly is secured in the hub in a position axially below and/or axially above the hub access opening.

17. The extension arm of claim 11, wherein the first and second arc shape clamp pieces include respective liners made of a material selected from polyolefins, polyesters, acetals, polyamides, fluorinated polymers, vinyls, acrylics, polycarbonates, polyimides, polysulphones, and blends and alloys thereof.

18. The extension arm of claim 11, wherein the first and second arc shape clamp pieces include unreinforced, semi-crystalline thermoplastic polyester based on polyethylene terephthalate (PET-P).

19. The extension arm of claim 11, wherein the first and second arc shape clamp pieces include respective first and second polymer liners made of UHMW-PE.

20. A method of installing a brake assembly in a medical device support system having a central shaft and an extension arm having a support for a medical device and a hub at its proximal end mounted to the central shaft for pivotable movement about the central shaft, the method comprising:
   providing first and second discrete arc shape clamp pieces of the brake assembly;
   inserting the first and second arc shape clamp pieces through a hub access opening in the hub of the extension arm;
   arranging the first and second arc shape clamp pieces relative to the central shaft to respectively increase and decrease a frictional braking force to the central shaft in response to flexural movement of the first and second arc shape clamp pieces; and,
   securing the brake assembly in the hub of the extension arm for rotation with the extension arm about the central shaft.

21. The method of claim 20, wherein the inserting includes inserting the first and second arc shape clamp pieces radially through the hub access opening until an inner liner abuts or nearly abuts the central shaft.

22. The method of claim 20, wherein the arranging includes rotating the first and second arc shape clamp pieces at least partially about the central shaft.

23. The method of claim 20, wherein the arranging includes moving the first and second arc shape clamp pieces to a position axially adjacent to the hub access opening.

24. The method of claim 20, wherein the arranging includes inserting first and second radially protruding tabs of the respective first and second arc shape clamp pieces into a radially protruding notch in the hub to a position axially adjacent to the hub access opening.

25. The method of claim 20, wherein the arranging includes sliding axially the first and second arc shape clamp pieces relative to one another.

* * * * *